(12) United States Patent
Clifford et al.

(10) Patent No.: US 9,532,804 B2
(45) Date of Patent: Jan. 3, 2017

(54) IMPLANTATION APPROACH AND INSTRUMENTALITY FOR AN ENERGY ABSORBING SYSTEM

(71) Applicant: Moximed, Inc., Hayward, CA (US)

(72) Inventors: Anton G. Clifford, Mountain View, CA (US); Josef L. Friedmann, Scotts Valley, CA (US); Michael E. Landry, Austin, TX (US); David Lowe, Redwood City, CA (US); Joshua Makower, Los Altos, CA (US); Mary O'Connell, Menlo Park, CA (US); Alan C. Regala, Seattle, WA (US); Michael Rode, Lake Oswego, OR (US); Clinton N. Slone, San Francisco, CA (US)

(73) Assignee: MOXIMED, INC., Hayward, CA (US)

( * ) Notice: Subject to any disclaimer, the term of this patent is extended or adjusted under 35 U.S.C. 154(b) by 0 days.

(21) Appl. No.: 14/206,082

(22) Filed: Mar. 12, 2014

(65) Prior Publication Data
US 2014/0277446 A1    Sep. 18, 2014

Related U.S. Application Data

(60) Provisional application No. 61/799,775, filed on Mar. 15, 2013.

(51) Int. Cl.
  *A61F 2/08* (2006.01)
  *A61B 17/56* (2006.01)
(52) U.S. Cl.
  CPC .......... *A61B 17/56* (2013.01); *A61B 2017/567* (2013.01)

(58) Field of Classification Search
  CPC ........ A61F 2/08; A61F 2/0805; A61F 2/0811; A61F 2/38; A61B 17/56; A61B 17/7028; A61B 17/70; A61B 2017/567
  See application file for complete search history.

(56) References Cited

U.S. PATENT DOCUMENTS

| | | | | |
|---|---|---|---|---|
| 4,036,335 A | * | 7/1977 | Thompson et al. | 188/282.9 |
| 4,054,955 A | * | 10/1977 | Seppo | 623/19.13 |
| 5,375,823 A | * | 12/1994 | Navas | 623/17.15 |
| 5,454,550 A | * | 10/1995 | Christopherson | 267/221 |
| 5,477,948 A | * | 12/1995 | Stevens | 267/221 |
| 5,672,175 A | * | 9/1997 | Martin | 606/86 A |
| 6,162,223 A | * | 12/2000 | Orsak et al. | 606/59 |
| 6,190,411 B1 | * | 2/2001 | Lo | 623/13.13 |
| 6,193,225 B1 | * | 2/2001 | Watanabe | 267/180 |
| 6,342,076 B1 | * | 1/2002 | Lundborg | 623/21.15 |
| 6,402,750 B1 | * | 6/2002 | Atkinson et al. | 606/279 |

(Continued)

FOREIGN PATENT DOCUMENTS

| EP | 2471496 | 7/2012 |
|---|---|---|
| WO | WO02/078554 | 10/2002 |

OTHER PUBLICATIONS

International Search Report and Written Opinion for PCT Patent App. No. PCT/US2014/024229 (Jul. 3, 2014).

*Primary Examiner* — Alvin Stewart
(74) *Attorney, Agent, or Firm* — Cermak Nakajima & McGowan LLP; Adam J. Cermak

(57) ABSTRACT

A system for manipulating energy transferred by members defining a joint and a method of implantation includes a first attachment structure configured to be attached to a first member of the joint and a second attachment structure configured to be attached to a second member of the joint.

9 Claims, 23 Drawing Sheets

(56) References Cited

U.S. PATENT DOCUMENTS

| | | | |
|---|---|---|---|
| 6,453,795 B1* | 9/2002 | Eicher et al. | 92/23 |
| 6,547,778 B1* | 4/2003 | Sklar et al. | 606/1 |
| 6,572,653 B1* | 6/2003 | Simonson | 623/17.13 |
| 7,029,475 B2* | 4/2006 | Panjabi | 606/279 |
| 7,291,150 B2* | 11/2007 | Graf | 606/86 A |
| 7,361,196 B2* | 4/2008 | Fallin et al. | 623/61 |
| 7,611,540 B2* | 11/2009 | Clifford et al. | 623/20.21 |
| 7,655,041 B2* | 2/2010 | Clifford et al. | 623/13.12 |
| 7,678,147 B2* | 3/2010 | Clifford et al. | 623/13.12 |
| 7,763,020 B2* | 7/2010 | Draper | 606/59 |
| 7,846,211 B2* | 12/2010 | Clifford et al. | 623/20.21 |
| 8,088,166 B2* | 1/2012 | Makower et al. | 623/20.14 |
| 8,100,967 B2* | 1/2012 | Makower et al. | 623/13.12 |
| 8,123,805 B2* | 2/2012 | Makower et al. | 623/13.12 |
| 8,409,281 B2* | 4/2013 | Makower et al. | 623/13.12 |
| 8,523,948 B2* | 9/2013 | Slone et al. | 623/18.11 |
| 8,709,090 B2* | 4/2014 | Makower et al. | 623/20.21 |
| 8,808,374 B2* | 8/2014 | Eggli | 623/13.14 |
| 8,821,507 B2* | 9/2014 | Axelson et al. | 606/99 |
| 9,034,049 B2* | 5/2015 | Slone et al. | 623/18.11 |
| 9,044,270 B2* | 6/2015 | Gabriel et al. | |
| 9,060,867 B2* | 6/2015 | Slone et al. | |
| 2002/0095154 A1* | 7/2002 | Atkinson et al. | 606/61 |
| 2002/0151978 A1* | 10/2002 | Zacouto et al. | 623/17.12 |
| 2005/0055025 A1* | 3/2005 | Zacouto et al. | 606/72 |
| 2005/0085815 A1* | 4/2005 | Harms et al. | 606/61 |
| 2005/0171543 A1* | 8/2005 | Timm et al. | 606/61 |
| 2005/0251260 A1* | 11/2005 | Gerber et al. | 623/17.13 |
| 2005/0288670 A1* | 12/2005 | Panjabi et al. | 606/61 |
| 2006/0064090 A1* | 3/2006 | Park | 606/61 |
| 2006/0064169 A1* | 3/2006 | Ferree | 623/17.12 |
| 2006/0247632 A1* | 11/2006 | Winslow et al. | 606/61 |
| 2007/0032123 A1* | 2/2007 | Timm et al. | 439/395 |
| 2007/0043356 A1* | 2/2007 | Timm et al. | 606/61 |
| 2007/0100341 A1* | 5/2007 | Reglos et al. | 606/61 |
| 2007/0112427 A1* | 5/2007 | Christy et al. | 623/17.11 |
| 2007/0161993 A1* | 7/2007 | Lowery et al. | 606/61 |
| 2007/0168033 A1* | 7/2007 | Kim et al. | 623/17.13 |
| 2007/0173822 A1* | 7/2007 | Bruneau et al. | 606/61 |
| 2007/0288094 A1* | 12/2007 | Krishna et al. | 623/17.15 |
| 2008/0275509 A1* | 11/2008 | Clifford et al. | 606/282 |
| 2008/0275552 A1* | 11/2008 | Makower et al. | 623/13.13 |
| 2008/0275555 A1* | 11/2008 | Makower et al. | 623/14.12 |
| 2008/0275556 A1* | 11/2008 | Makower et al. | 623/18.11 |
| 2008/0275557 A1* | 11/2008 | Makower et al. | 623/18.11 |
| 2008/0275558 A1* | 11/2008 | Clifford et al. | 623/20.14 |
| 2008/0275559 A1* | 11/2008 | Makower et al. | 623/20.14 |
| 2008/0275560 A1* | 11/2008 | Clifford et al. | 623/20.15 |
| 2008/0275561 A1* | 11/2008 | Clifford et al. | 623/20.21 |
| 2008/0275562 A1* | 11/2008 | Clifford et al. | 623/20.21 |
| 2008/0275563 A1* | 11/2008 | Makower et al. | 623/20.21 |
| 2008/0275564 A1* | 11/2008 | Makower et al. | 623/20.21 |
| 2008/0275565 A1* | 11/2008 | Makower et al. | 623/20.22 |
| 2008/0275571 A1* | 11/2008 | Clifford et al. | 623/46 |
| 2009/0012521 A1* | 1/2009 | Axelson et al. | 606/53 |
| 2009/0014016 A1* | 1/2009 | Clifford et al. | 128/898 |
| 2009/0018656 A1* | 1/2009 | Clifford et al. | 623/14.12 |
| 2009/0018665 A1* | 1/2009 | Clifford et al. | 623/18.11 |
| 2009/0048631 A1* | 2/2009 | Bhatnagar et al. | 606/246 |
| 2009/0099608 A1* | 4/2009 | Szczesny | 606/257 |
| 2009/0275945 A1* | 11/2009 | Makower et al. | 606/60 |
| 2009/0276054 A1* | 11/2009 | Clifford et al. | 623/20.21 |
| 2009/0318976 A1* | 12/2009 | Gabriel et al. | 606/283 |
| 2010/0087862 A1* | 4/2010 | Biedermann et al. | 606/259 |
| 2010/0114322 A1* | 5/2010 | Clifford et al. | 623/20.14 |
| 2010/0121457 A1* | 5/2010 | Clifford et al. | 623/20.21 |
| 2010/0137996 A1* | 6/2010 | Clifford et al. | 623/23.41 |
| 2010/0145449 A1* | 6/2010 | Makower et al. | 623/13.14 |
| 2010/0211104 A1* | 8/2010 | Moumene et al. | 606/257 |
| 2011/0060422 A1* | 3/2011 | Makower et al. | 623/46 |
| 2011/0071643 A1* | 3/2011 | Clifford et al. | 623/20.21 |
| 2011/0093079 A1* | 4/2011 | Slone et al. | 623/18.11 |
| 2011/0093080 A1* | 4/2011 | Slone et al. | 623/20.14 |
| 2011/0112639 A1* | 5/2011 | Regala et al. | 623/13.12 |
| 2011/0137415 A1* | 6/2011 | Clifford et al. | 623/13.14 |
| 2011/0144646 A1* | 6/2011 | Windolf | 606/70 |
| 2011/0238119 A1* | 9/2011 | Moumene et al. | 606/264 |
| 2012/0022655 A1* | 1/2012 | Clifford | 623/18.11 |
| 2012/0053644 A1* | 3/2012 | Landry et al. | 606/86 R |
| 2012/0116522 A1* | 5/2012 | Makower et al. | 623/18.11 |
| 2012/0136449 A1* | 5/2012 | Makower et al. | 623/18.11 |
| 2012/0179273 A1* | 7/2012 | Clifford et al. | 623/46 |
| 2012/0253414 A1* | 10/2012 | Gabriel et al. | 606/86 R |
| 2012/0296434 A1* | 11/2012 | Kumar | 623/18.11 |
| 2013/0013066 A1* | 1/2013 | Landry et al. | 623/14.12 |
| 2013/0013067 A1* | 1/2013 | Landry et al. | 623/14.12 |
| 2013/0041416 A1* | 2/2013 | Regala et al. | 606/86 R |
| 2013/0041464 A1* | 2/2013 | Regala et al. | 623/13.11 |
| 2013/0041465 A1* | 2/2013 | Regala et al. | 623/13.12 |
| 2013/0138218 A1* | 5/2013 | Landry et al. | 623/20.14 |
| 2013/0197638 A1* | 8/2013 | Clifford et al. | 623/13.12 |
| 2013/0197639 A1* | 8/2013 | Clifford et al. | 623/13.14 |
| 2013/0211454 A1* | 8/2013 | Beger et al. | 606/255 |
| 2013/0211521 A1* | 8/2013 | Shenoy et al. | 623/13.12 |
| 2013/0218272 A1* | 8/2013 | Clifford et al. | 623/13.12 |
| 2013/0304208 A1* | 11/2013 | Clifford et al. | 623/13.12 |
| 2013/0325122 A1* | 12/2013 | Gabriel et al. | 623/13.12 |
| 2013/0325123 A1* | 12/2013 | Clifford et al. | 623/13.12 |
| 2014/0088652 A1* | 3/2014 | Brown et al. | 606/286 |
| 2014/0142698 A1* | 5/2014 | Landry et al. | 623/14.12 |
| 2014/0156021 A1* | 6/2014 | Makower et al. | 623/23.41 |
| 2014/0172097 A1* | 6/2014 | Clifford et al. | 623/14.12 |
| 2014/0257292 A1* | 9/2014 | Embleton et al. | 606/71 |
| 2014/0257501 A1* | 9/2014 | Lowe et al. | 623/20.22 |
| 2014/0277445 A1* | 9/2014 | Slone et al. | 623/13.12 |
| 2014/0277446 A1* | 9/2014 | Clifford et al. | 623/13.12 |
| 2014/0358231 A1* | 12/2014 | Landry et al. | 623/14.12 |

* cited by examiner

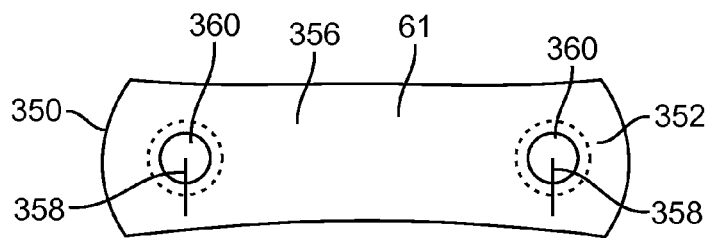
FIG. 36
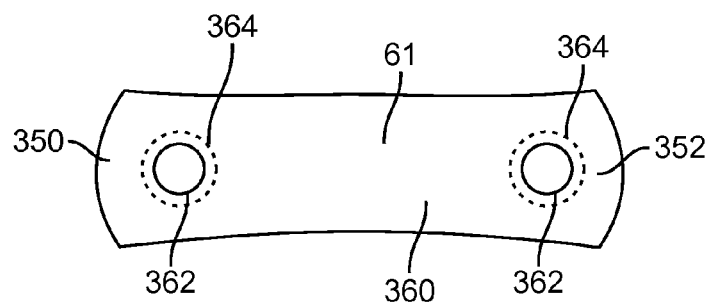
FIG. 37
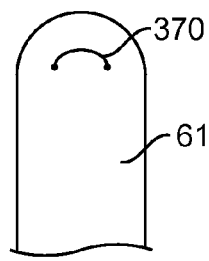 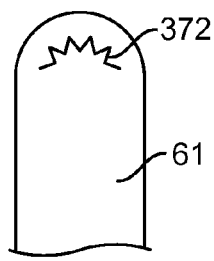 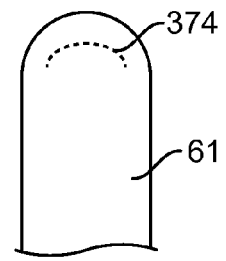
FIG. 38A     FIG. 38B     FIG. 38C
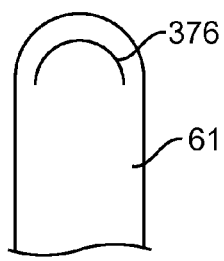 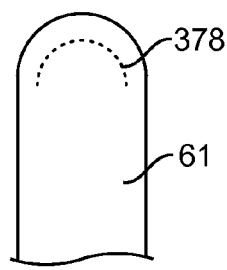
FIG. 38D     FIG. 38E

IMPLANTATION APPROACH AND INSTRUMENTALITY FOR AN ENERGY ABSORBING SYSTEM

This application claims priority under 35 U.S.C. §119 to U.S. Provisional App. No. 61/799,775, filed 15 Mar. 2013, the entirety of which is incorporated by reference herein.

BACKGROUND

Field of Endeavor

The present disclosure is directed towards an implantable device and related method, and more particularly to a surgical procedure for implanting an energy absorbing system for treating joint members.

Brief Description of the Related Art

Joint replacement is one of the most common and successful operations in modern orthopedic surgery. It consists of replacing painful, arthritic, worn or diseased parts of a joint with artificial surfaces shaped in such a way as to allow joint movement. Osteoarthritis is a common diagnosis leading to joint replacement. Such procedures are a last resort treatment as they are highly invasive and require substantial periods of recovery. Total joint replacement, also known as total joint arthroplasty, is a procedure in which all articular surfaces at a joint are replaced. This contrasts with hemiarthroplasty (half arthroplasty) in which only one bone's articular surface at a joint is replaced and unincompartmental arthroplasty in which the articular surfaces of only one of multiple compartments at a joint (such as the surfaces of the thigh and shin bones on just the inner side or just the outer side at the knee) are replaced. Arthroplasty as a general term, is an orthopedic procedure which surgically alters the natural joint in some way. This includes procedures in which the arthritic or dysfunctional joint surface is replaced with something else, procedures which are undertaken to reshape or realigning the joint by osteotomy or some other procedure. As with joint replacement, these other arthroplasty procedures are also characterized by relatively long recovery times and their highly invasive procedures. A previously popular form of arthroplasty was interpositional arthroplasty in which the joint was surgically altered by insertion of some other tissue like skin, muscle or tendon within the articular space to keep inflammatory surfaces apart. Another previously done arthroplasty was excisional arthroplasty in which articular surfaces were removed leaving scar tissue to fill in the gap. Among other types of arthroplasty are resection(al) arthroplasty, resurfacing arthroplasty, mold arthroplasty, cup arthroplasty, silicone replacement arthroplasty, and osteotomy to affect joint alignment or restore or modify joint congruity. When it is successful, arthroplasty results in new joint surfaces which serve the same function in the joint as did the surfaces that were removed. Any chondrocytes (cells that control the creation and maintenance of articular joint surfaces), however, are either removed as part of the arthroplasty, or left to contend with the resulting joint anatomy. Because of this, none of these currently available therapies are chondro-protective.

A widely-applied type of osteotomy is one in which bones are surgically cut to improve alignment. A misalignment due to injury or disease in a joint relative to the direction of load can result in an imbalance of forces and pain in the affected joint. The goal of osteotomy is to surgically re-align the bones at a joint and thereby relieve pain by equalizing forces across the joint. This can also increase the lifespan of the joint. When addressing osteoarthritis in the knee joint, this procedure involves surgical re-alignment of the joint by cutting and reattaching part of one of the bones at the knee to change the joint alignment, and this procedure is often used in younger, more active or heavier patients. Most often, high tibial osteotomy (HTO) (the surgical re-alignment of the upper end of the shin bone (tibia) to address knee malalignment) is the osteotomy procedure done to address osteoarthritis and it often results in a decrease in pain and improved function. However, HTO does not address ligamentous instability—only mechanical alignment. HTO is associated with good early results, but results deteriorate over time.

Other approaches to treating osteoarthritis involve an analysis of loads which exist at a joint. Both cartilage and bone are living tissues that respond and adapt to the loads they experience. Within a nominal range of loading, bone and cartilage remain healthy and viable. If the load falls below the nominal range for extended periods of time, bone and cartilage can become softer and weaker (atrophy). If the load rises above the nominal level for extended periods of time, bone can become stiffer and stronger (hypertrophy). Finally, if the load rises too high, then abrupt failure of bone, cartilage and other tissues can result. Accordingly, it has been concluded that the treatment of osteoarthritis and other bone and cartilage conditions is severely hampered when a surgeon is not able to precisely control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there is a need for devices which facilitate the control of load on a joint undergoing treatment or therapy, to thereby enable use of the joint within a healthy loading zone.

Certain other approaches to treating osteoarthritis contemplate external devices such as braces or fixators which attempt to control the motion of the bones at a joint or apply cross-loads at a joint to shift load from one side of the joint to the other. A number of these approaches have had some success in alleviating pain but have ultimately been unsuccessful due to lack of patient compliance or the inability of the devices to facilitate and support the natural motion and function of the diseased joint. The loads acting at any given joint and the motions of the bones at that joint are unique to the body that the joint is a part of. For this reason, any proposed treatment based on those loads and motions must account for this variability to be universally successful. The mechanical approaches to treating osteoarthritis have not taken this into account and have consequently had limited success.

Certain prior approaches to treating osteoarthritis have also failed to account for all of the basic functions of the various structures of a joint in combination with its unique movement. In addition to addressing the loads and motions at a joint, an ultimately successful approach must also acknowledge the dampening and energy absorption functions of the anatomy, and be implantable via a minimally invasive technique. Prior devices designed to reduce the load transferred by the natural joint typically incorporate relatively rigid constructs that are incompressible. Mechanical energy (E) is the action of a force (F) through a distance (s) (i.e., $E=F^x s$). Device constructs which are relatively rigid do not allow substantial energy storage as the forces acting on them do not produce substantial deformations—do not act through substantial distances—within them. For these relatively rigid constructs, energy is transferred rather than stored or absorbed relative to a joint. By contrast, the natural joint is a construct comprised of elements of different compliance characteristics such as bone, cartilage, synovial fluid, muscles, tendons, ligaments, etc. as described above. These dynamic elements include relatively compliant ones (ligaments, tendons, fluid, cartilage) which allow for substantial energy absorption and storage, and relatively stiffer ones (bone) that allow for efficient energy transfer. The cartilage in a joint compresses under applied force and the resultant force displacement product represents the energy absorbed by cartilage. The fluid content of cartilage also acts to stiffen its response to load applied quickly and dampen its response to loads applied slowly. In this way, cartilage acts to absorb and store, as well as to dissipate energy.

Approaches for surgically implanting extra-articular mechanical energy absorbing apparatus have been developed. As precise and effective placement are critical to the efficacy of an implanted extra-articular mechanical absorbing apparatus, further advancements in patient preparation and device-to-anatomy juxtapositional relationships have been found to be both useful and necessary.

With the foregoing applications in mind, it has been found to be necessary to develop effective structures for mounting to body anatomy. Such structures should conform to body anatomy and cooperate with body anatomy to achieve desired load reduction, energy absorption, energy storage, and energy transfer.

Furthermore, there is a need for the development of low or reduced profile implant components, while endeavoring to eliminate fatigue failure risks. Additionally, it has been found to be desirable to develop a streamlined and repeatable surgical implantation technique involving reduced fluoroscopy time and incision sizes. It is also desirable to provide apparatus and approaches aimed at treating larger patient populations.

For these implant structures to function optimally, they must not cause an adverse disturbance to joint motion. Therefore, what is needed is a refined surgical approach to implanting a device which addresses both joint movement and varying loads as well as complements underlying or adjacent anatomy.

The present disclosure satisfies these and other needs.

SUMMARY

Briefly and in general terms, the present disclosure is directed towards treating diseased or mal-aligned body joints, typically affected by osteoarthritis, using an adjustable energy absorbing system without limiting the range of motion of the patient's articulating joint. The energy absorbing system provides forces in direction opposite that of ligament spanning body joints. The system includes an energy absorber having a first attachment structure configured to be attached to and articulate with respect to a first member of the joint and a second attachment structure configured to be fixed relative to a second member of the joint. The devices of the present invention accomplish one or more of: absorbing energy during normal gait, reducing load on at least a portion of the natural joint, load transferring or bypassing, energy cushioning, and load sharing or redistribution. Further, the particular anatomy of a patient is considered in the contemplated approaches in that loads on desired portions of anatomy are manipulated without overloading healthy surfaces. In a preferred embodiment, the present invention adds an energy absorber to the joint to reduce energy transferred through the natural joint. One embodiment includes a system for manipulating or absorbing energy transferred by members defining a joint. This system may be used to treat anatomy affected with osteoarthritis.

In one particular approach, there is contemplated an extra-articular implantable energy absorbing system for treating a joint defined by a first bone and a second bone. The joint can be the knee joint defined by the femur and tibia bones. The system can include a first base component affixed to a first bone and a second base component affixed to a second bone. A first mount is attached to the first bone and a second mount is attached to the second bone. Further, an energy absorbing assembly connects to the first and second mounts and spans across the joint. Springs can be included to provide energy absorbing functions. In one specific assembly, three springs are employed as part of the energy absorbing structure. Bases with cone-like projections receive a spherical bearing, about which is socket formed at ends of the energy absorbing assembly are configured.

The present disclosure is also directed towards a surgical procedure for implanting a medical device. More particularly, the procedure involves placement of an extra-articular mechanical energy absorbing apparatus across anatomy being treated. In one aspect, the energy absorbing apparatus is placed across an articulating joint.

In one embodiment, the contemplated approach involves one or more of patient preparation, identification of device position relative to anatomy, structure of proper device components and device implantation. Various devices and implantation aids are disclosed to accomplish effective and proper placement of a medical device.

In one contemplated approach, the position of the patient and treatment areas are selected for easy access and to achieve proper alignment at an implantation site. In various contemplated approaches, guide structures are configured adjacent a treatment site to aid in identifying a proper juxtapositional relationship between patient body anatomy and mechanical energy absorbing apparatus. In one particular aspect, guide structures can be embodied in a multi-directional center of rotation locator configured to identify a center of rotation of an articulating limb. Further, remote visualization as well as templates are contemplated for use in identifying device-to-anatomy mounting locations and incision sites. Also, anatomical references can be used to locate the center of rotation, and the target location can be manually positioned by referencing these anatomical references.

In further contemplated approaches, proper size and configuration of components of the mechanical energy absorbing apparatus involves understanding the anatomy of the treatment area as well as the unique characteristics of the anatomy of the patient. When the energy absorbing apparatus includes one or more bases which are to be fixed to a bone, such bases are selected to provide surfaces which approximate the bone to which it is to be attached and includes desired separation from the bone to provide connecting structure. In this regard, remote sizing devices and a direct physical inspection of the anatomy is undertaken. Furthermore, base locating tools are employed to facilitate both selection of base implantation sites and proper component identification.

Structures are used to identify and initiate device mounting and act as drill guides. Also, tools are provided to connect various components of an energy absorbing apparatus at the treatment site. Kirscher wires (K-wires) and Steinmann pins are employed to help maintain alignment of components within the interventional site. In the art, "Kirscher wire" or "K-wire" is generally used to refer to wires up to 2 mm in diameter. "Steinmann pin" is generally used to refer to wires above 2 mm in diameter. For the purpose of this application, the term "K-wire" is used generically to cover both Kirscher wires and Steinmann pins. Both compression and locking screws are contemplated for fixation purposes.

Moreover, an elongated tunneling tool is contemplated to form a tunnel or other access area at an interventional site. Devices and approaches are also contemplated for advancing components through the tunnel formed below a patient's skin and for both temporary fixation and permanent assembly of parts. Post-implanted and post operative examination is also contemplated to ensure proper operation of the mechanical absorbing device.

The mechanical energy absorbing apparatus has the capacity to absorb energy in addition to transfer energy from the joint. Various joints of the body can be treated employing the systems and methods of the present invention. In particular, articulating bones involved in synovial joints can benefit from the present invention. Accordingly, there are contemplated applications to the joints in the knee, ankle, shoulder, hip, hand, wrist, elbow, mandible, and foot.

In one specific embodiment, the presently disclosed apparatus is embodied in a device utilizing an element, or elements functioning as a unit, which responds to bending or changes in elongation. Further, the device is used to reduce the loading experienced by the articular surfaces of the tibiofemoral joint. In one embodiment, the device is designed to reduce load on the joint during knee extension with energy absorption. Joint load reduction in this phase is governed by the compression of the device—increased compression yields greater joint reduction. The device is anchored in a position which ensures device elongation resulting from knee flexion. As the knee moves into flexion, the device is un-compressed and will cause little to no joint load changes. The device may have other features which ensure correct device alignment, and prevent against buckling, as the device transitions into a compressed state. The device can also be configured to provide joint load reductions during flexion or throughout the nearly full range of motion.

Other features of the energy absorbing system and device will become apparent from the following detailed description, taken in conjunction with the accompanying drawings, which illustrate, by way of example, the principles of the embodiments.

BRIEF DESCRIPTION OF THE DRAWINGS

FIG. 36 is a front view, depicting a sheath;

FIG. 37 is a back view, depicting the sheath of FIG. 36;

FIG. 38A-E are side views, depicting various approaches to sealing the sheath of FIGS. 36 and 37;

DETAILED DESCRIPTION OF EXEMPLARY EMBODIMENTS

Figure 1A:
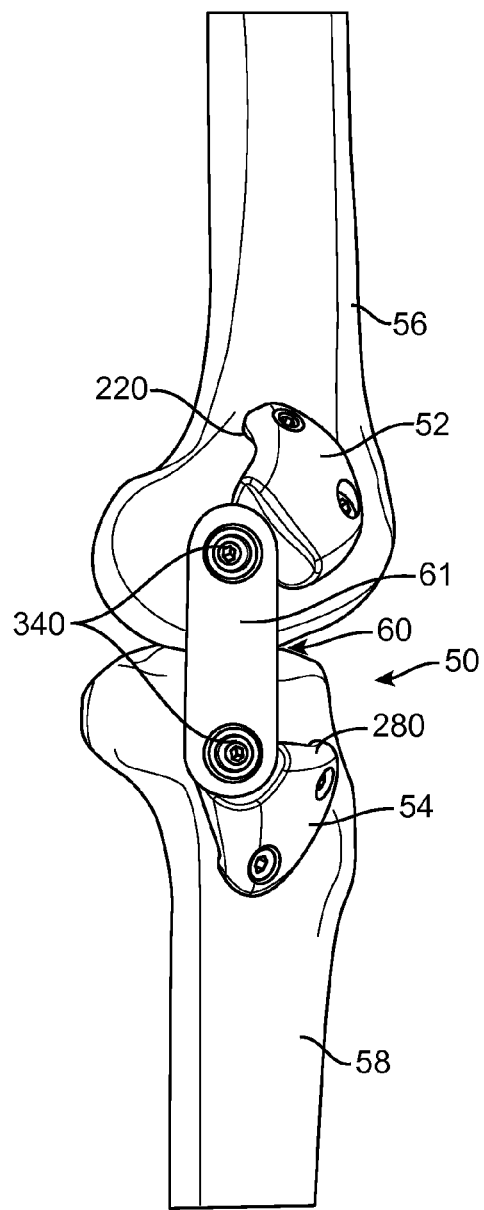
FIG. 1A is a side view, depicting an extra-articulating implantable mechanical energy absorbing system.

Referring now to the drawings, which are provided by way of example and not limitation, the present disclosure is directed towards apparatus for treating body tissues. In applications relating to the treatment of body joints, the described approach seeks to alleviate pain associated with the function of diseased or malaligned members forming a body joint. Whereas the present invention is particularly suited to address issues associated with osteoarthritis, the energy manipulation accomplished by the present invention lends itself well to broader applications. Moreover, the present invention is particularly suited to treating synovial joints such as the knee, finger, wrist, ankle, hip and shoulder.

In one particular aspect, the presently disclosed method seeks to permit and complement the unique articulating motion of the members defining a body joint of a patient while simultaneously manipulating energy being experienced by both cartilage and osseous tissue (cancellous and cortical bone). Approaches involving varying energy absorption and transfer during the rotation of the joint and selecting a geometry for the energy absorption assembly to provide necessary flexibility are implemented into various embodiments of the present invention. Certain of the embodiments include geometry which accomplishes variable energy absorption designed to minimize and complement the dampening effect and energy absorption provided by the anatomy of the body, such as that found at a body joint. It has been postulated that to minimize pain, in an osteoarthritic joint absorption of 1-40% of forces, in varying degrees throughout the motion of the joint, may be necessary. Variable absorption in the range of 5-20% can be a target for certain applications. In certain specific applications, temporary distraction (e.g., less than 3 months) is employed in the energy manipulation approach.

Conventional or surgical or minimally invasive approaches are taken to gain access to a body joint or other anatomy requiring attention. Arthroscopic approaches are thus contemplated when reasonable to both implant the energy manipulation assembly as well as to accomplish adjusting an implanted assembly. Moreover, biologically inert materials of various kinds can be employed in constructing the energy manipulation assemblies of the present invention.

In one approach for treating a knee, an implantable extra-articular energy absorber system is designed to reduce medial compartment loads of the knee. The absorber system is comprised of two contoured base components, a kinematic load absorber and a set of bone screws. The implanted system is both extra articular and extra capsular and resides in the subcutaneous tissue on the medial aspect of the knee. The device is inserted through two small incisions superior to the medial femoral condyle and inferior to the tibial plateau. The contoured base components are fixed to the medial cortices of the femur and tibia using bone screws.

The femoral and tibial base components are contoured to ensure optimal fit to the bony surfaces and can be plasma sprayed and/or coated with hydroxyapatite on bone contacting surfaces to promote bony ingrowth and enhance osteointegration. Base material is provided as a transition surface from bone to the system. Thus, bases are provided with thickness and curvature to purposefully alter geometry of the base to improve aesthetics. The orthopedic bone screws provide immediate fixation of the base components to the bone during osteointegration.

The kinematic absorber is attached to the base components between two bearing and socket joints. The range of motion of the components of the system can be determined by the bearing/socket geometry, base/absorber geometry and relative position of the base to absorber at final implantation. The absorber is comprised of three helically wound springs two on spring guides and the third configured about a piston and tube arrangement. The springs act to absorb load from the medial compartment of the knee while the ball/sockets allow the device to accommodate full knee range of motion.

A plane of the horizon of the femoral and tibial bearings are important relative to the motions of the knee and the implantable system. If the bearing horizon resides in an inappropriate plane then one of the ball/sockets can have insufficient motion in at least one direction. The plane of the bearing is defined by the position of a base cone on the bone. This is predetermined by the cone design and its trajectory. Setting the trajectory of the femoral and tibial cones is achieved using instrumentation during placement of reference K-wires. It is to be recognized the relative trajectories of the cone axis change during knee motions. It is also to be noted that the length of the absorber is important with respect to a tibial bearing screw. A defined target region on the femur can be required for device functionality as can be a minimum distance a most proximal tibial screw needs to be from a tibial plateau for strength and prevention of joint space violation. The absorber can be a length greater than the distance of a femoral pivot to a femoral articular surface across joint space and to a tibial pivot screw.

The extent of varus/valgus rotation of the knee increases with flexion, being low at full extension and relatively high at high flexion. The currently contemplated socket can be designed to also have increasing varus/valgus range of motion with flexion Moreover, the kinematics of femoral and tibial articulations can be very different during knee motions. Identical ball/sockets arrangements can be provided on both sides of a knee joint but different arrangements are also contemplated.

It has been observed that the greatest lengthening of the absorber can occur at deep flexion under valgus stress with an external tibial rotation. The lengthening in this physiological position if contemplated to be less than would allow disassociation of parts of the absorber.

The load bypassing knee support system is indicated for patients suffering with medial knee pain secondary to osteoarthritis who have failed medical treatments.

It is contemplated that the absorber system is supplied packaged in a set of individually sealed Tyvek/film pouches. The base components and absorber assemblies will each be individually packaged and labeled. Moreover, the load bypassing knee support system and all its components are provided sterile and are not intended for reuse/re-sterilization by the user. These devices are sterilized using ethylene oxide (EtO). Surgical instruments, positioning and locking instruments must be sterilized using normal hospital orthopedic instrument sterilization methods.

The energy absorber having a spring value of about twenty pounds can provide therapeutic benefit for patients of 275 pounds or less. Higher spring forces would provide greater reduction in joint load and may correlate to greater symptom (i.e., pain) relief.

It has been recognized that knee forces have multiple components. There are a quadriceps force $F_Q$ and a ground reaction force $F_G$ directed generally longitudinally along a leg and there are lateral compartment forces $F_L$ and medial compartment forces $F_M$. There is, however, no conventional clinical measure of $F_M$ or $F_L$. On the other hand, there are non-axial knee forces which result in a moment being applied across the joint referred to as a knee adduction moment. The knee adduction moment (KAM) can be measured clinically. The measurements are useful as KAM can be considered to be a clinical surrogate measure for knee forces.

It has been further observed that a high knee adduction moment correlates with pain. That is, it would be expected that a group of people with diseased joints having lower KAM may not have pain whereas individuals with a relatively higher KAM would experience pain. Thus, an active reduction of knee adduction moment can reduce pain. The system of the present invention reduces the KAM of the patient.

It has also been found that a medial compartment of a knee of an average person with osteoarthritis can benefit from an absorber set for compression between 1 mm and 10 mm, and preferably 3-6 mm with a spring or absorber element that accommodates a range from 20-60 pounds. In a preferred embodiment, the absorber is set for about 4 mm of such compression and a pre-determined load of about 10-50 pounds, preferably about 30 pounds.

Moreover, each of the contemplated embodiments can include three springs machined to provide desirable energy absorbing which varies as the spring is compressed during various degrees of flexion and extension of joint markers to which the energy absorbing device is attached. The term "spring" is used throughout the description but it is contemplated to include other energy absorbing and compliant structures can be used to accomplish the functions of the invention as described in more detail below. Additionally, any of the various disclosed approaches to achieving adjustment through a patient's skin, either through direct engagement with the energy absorbing device with a tool or by applying forces to the device through the surface of the skin can be incorporated to fill a perceived need.

In certain situations, it has been found to be a benefit to implant the energy absorbing device in an inactivated condition, only later taking steps, perhaps several weeks later, to place the device into an activated state. In this way, the device can become further affixed to bone as the bone and surrounding tissue grows over portions of the device. Accordingly, each of the disclosed embodiments can include structure so that after implantation, they can be later activated and adjusted through a patient's skin.

Figure 1B:
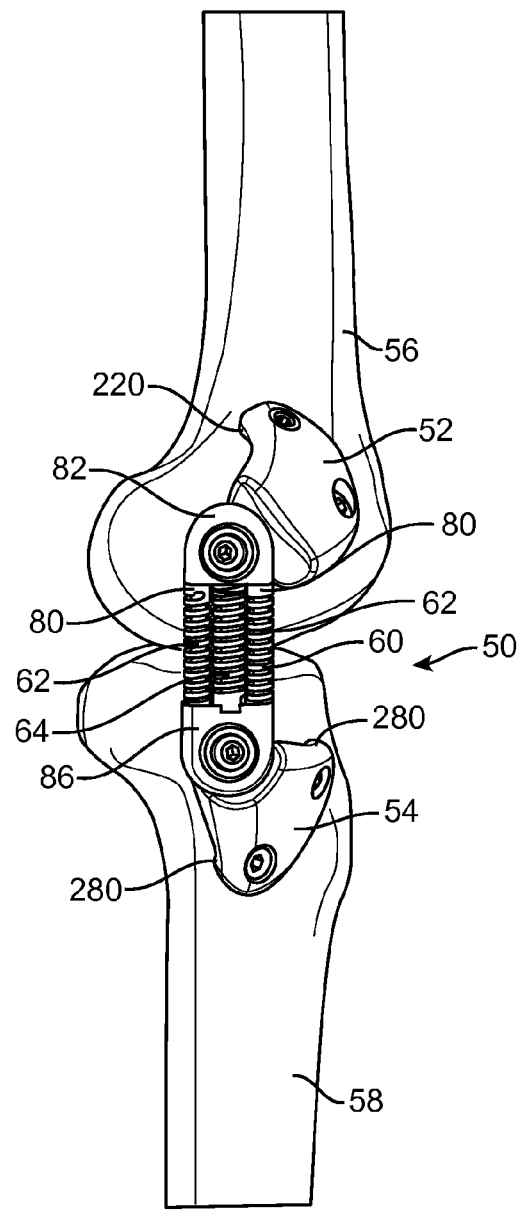
FIG. 1B is a side view, depicting the energy absorbing system of FIG. 1A with the sheath removed.
Figure 2:
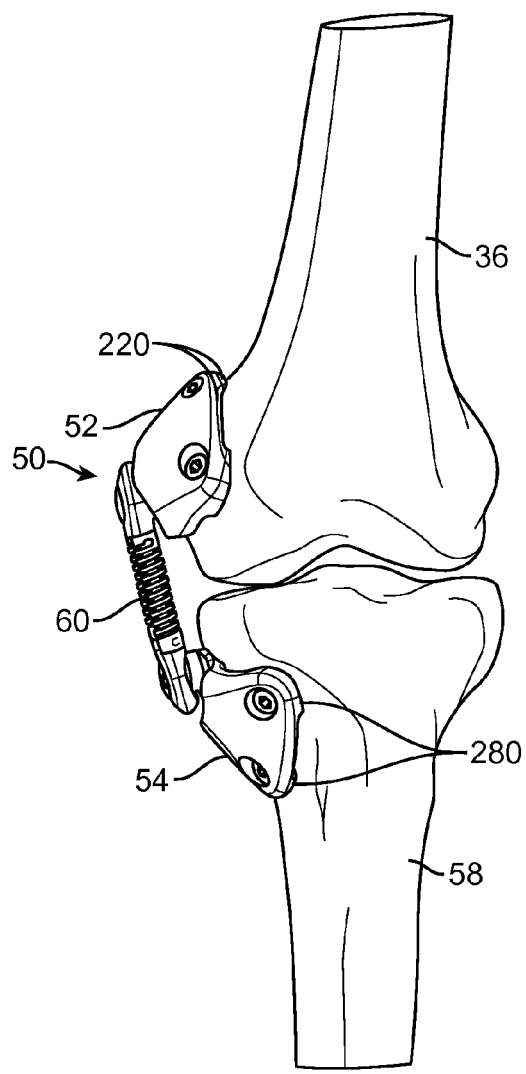
FIG. 2 is a front view, depicting the system of FIG. 1.
Figure 3:
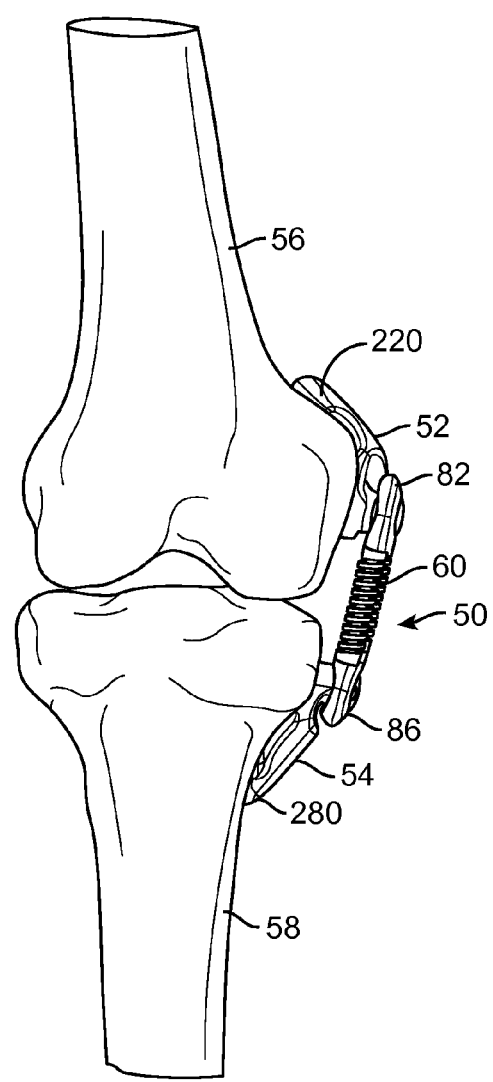
FIG. 3 is a rear view, depicting the system of FIG. 1B.

Referring now to FIGS. 1A-3, one embodiment of an energy absorbing system 50 is shown with proximal 52 and distal 54 base components positioned upon first 56 and second 58 members, respectively of a typical body joint. Here, the terminal end portions of the femur and tibia are depicted without surrounding tissue. It is noted that portions of the base components are contoured to match potential mounting surfaces of the femur and tibia. Also shown is an energy absorbing device 60 that is configured between and mounted to the base components. In FIG. 1A, the energy absorbing system 60 is shown with a sheath 61 which covers internal components. For viewing purposes the sheath 61 is omitted from other Figures. The details of the sheath 61 are presented below. The energy absorbing system has the capacity to absorb energy in addition to transfer energy from the joint. The energy absorption of the three springs can be expressed as the product of force and displacement. FIGS. 1-3 shows the knee joint at full extension with load being applied to springs 62, 64 of the energy absorbing device.

Figure 4:
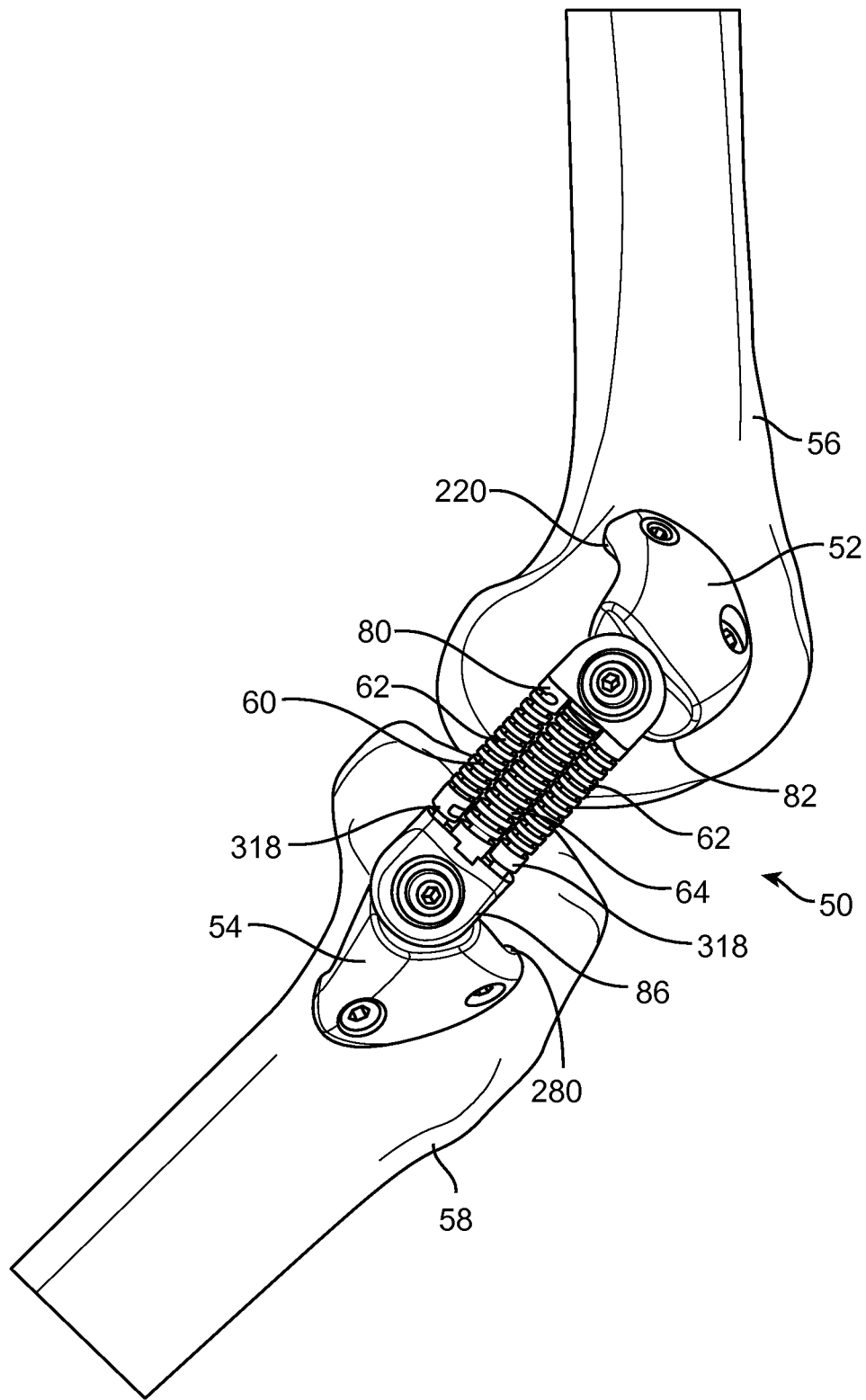
FIG. 4 is a side view, depicting the system of FIG. 1B attached to bones forming a 45° angle.
Figure 5:
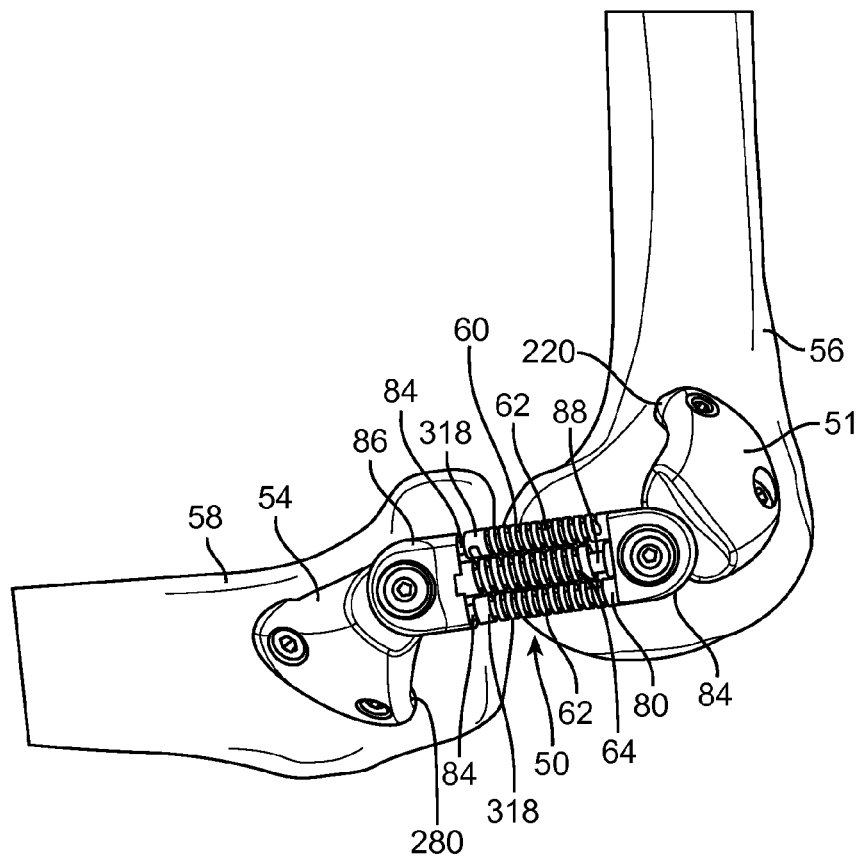
FIG. 5 is a side view, depicting the system of FIG. 1B attached to the bones forming a 90° angle.
Figure 6:
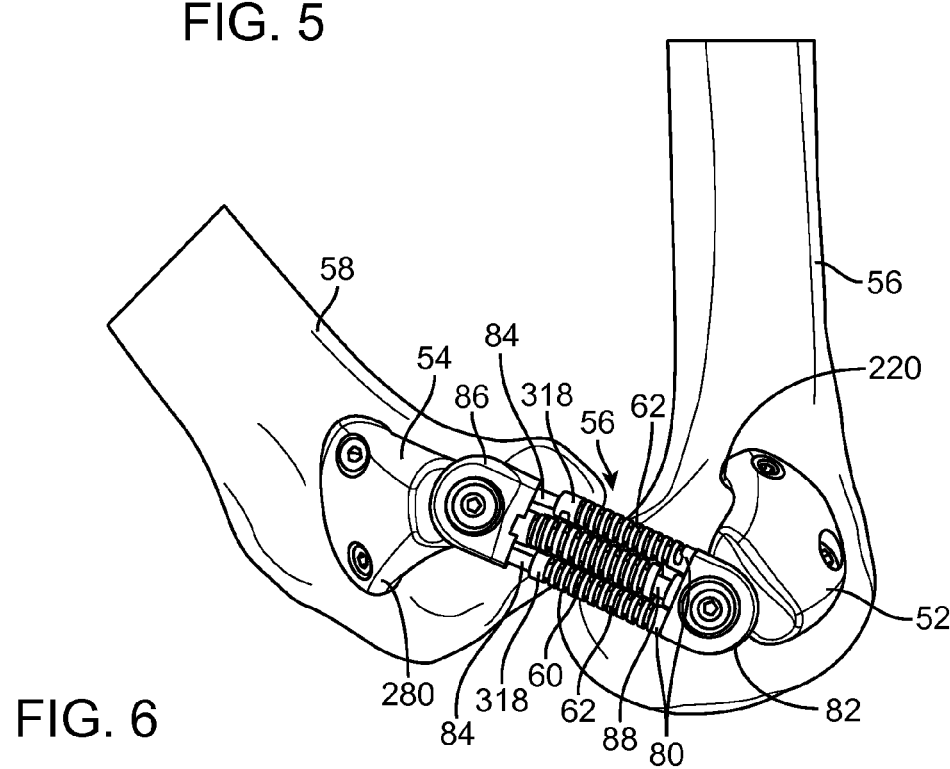
FIG. 6 is a side view, depicting the system of FIG. 1B attached to the bones forming a 140° angle.

FIG. 4 shows the knee joint flexed to 45° with zero load being applied to the spring and FIGS. 5 and 6 depict the knee joint flexed 90° and 140°; respectively, where zero load is also applied. The energy absorbing device lengthens as the knee swings from full extension to flexion and subsequently shortens as the knee swings from flexion to full extension such that the springs begin to be compressed between the ends of the device to absorb the load that the knee articulating surfaces normally would experience. The energy absorbing device and base components are mounted across the joint such that once the spring has achieved a predetermined amount of compression, and therefore load, the articulating surfaces of the knee then begin to carry the load in combination with the energy absorbing device such that the energy absorbing device does not "bottom out". The various energy absorbing devices in the present application are shown without a protective covering or sheath but it is contemplated that they can be within a protective covering or sheath to protect the moving elements from impingement by surrounding tissues and to prevent the devices from damaging surrounding tissue.

Still referring to FIGS. 1A-3, as well as FIGS. 4-6, one embodiment of an energy absorbing device 60 includes three machined springs 62, 64. The smaller, outer springs 62 each include a first end 80 which abuts and which is affixed to a first socket 82. These springs are also each configured about guides 84 projecting from a second socket 86 (See FIGS. 5 and 6). The larger middle spring 64 is fixed at one end to the second socket 86 and is further configured about a piston and tube arrangement 88 (See FIGS. 5 and 6). Further details of the energy absorbing device are presented below.

Figure 7:
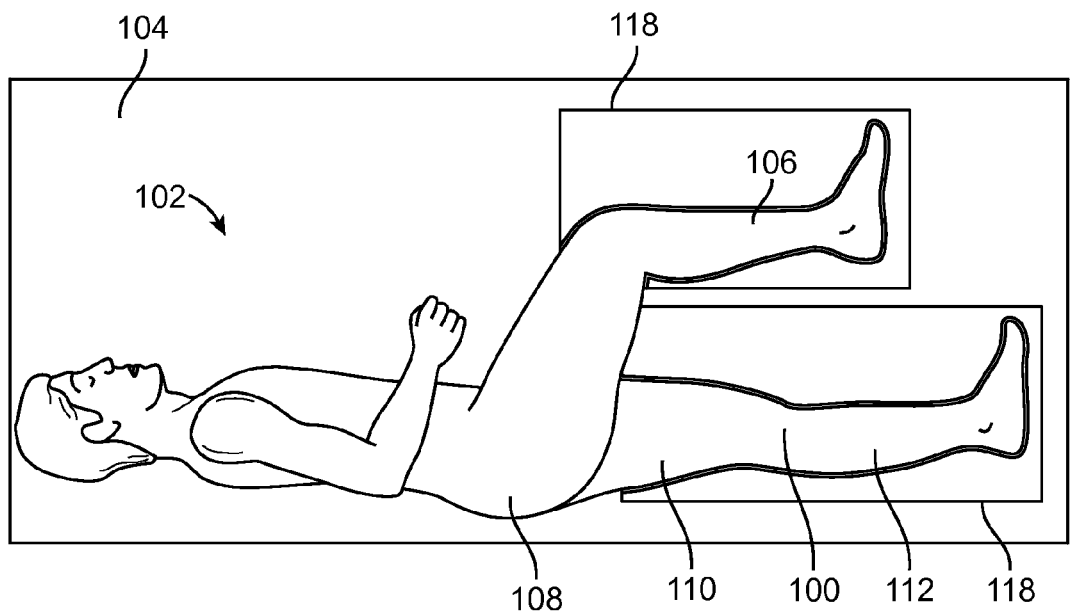
FIG. 7 is a perspective view, depicting a patient position for an interventional procedure.
Figure 8:
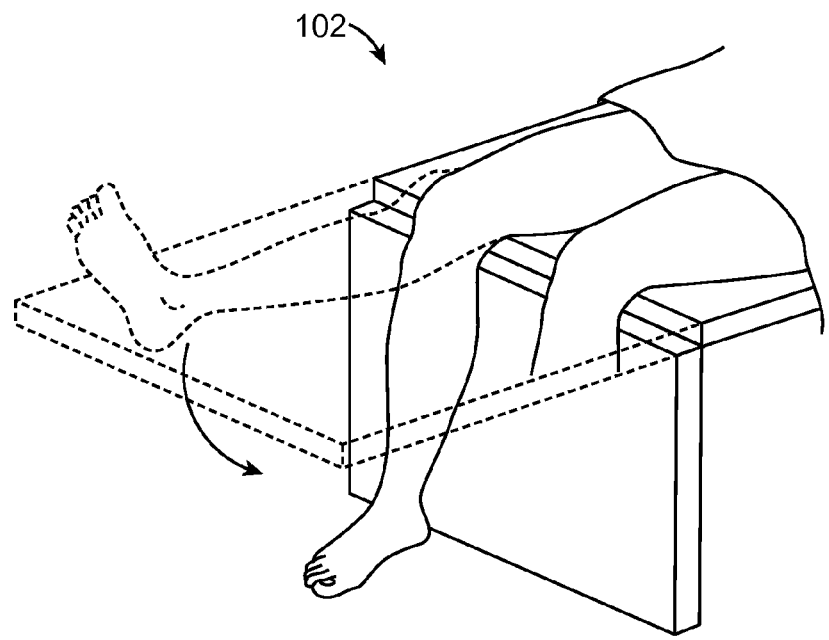
FIG. 8 is a perspective view, depicting an alternative positioning for a patient.

We now turn to one approach to an implantable procedure. For such a procedure, the patient 102 is placed upon a surgical table 104 in a lateral decubitus position with the patient 102 laying generally on his or her side as shown in FIG. 7. Alternatively, depending on surgeon preference, the patient can be placed in a supine position with an ability to flex the knee (See FIG. 8).

Figure 9:
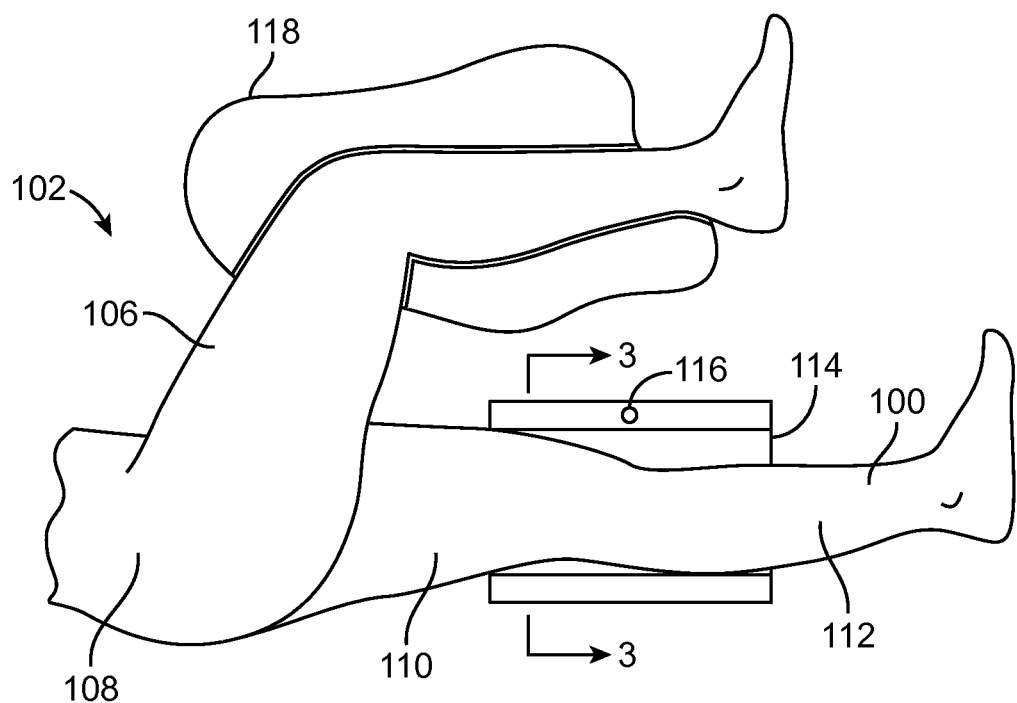
FIG. 9 is a perspective view, depicting an alternate approach for securing a limb of a patient.
Figure 10:
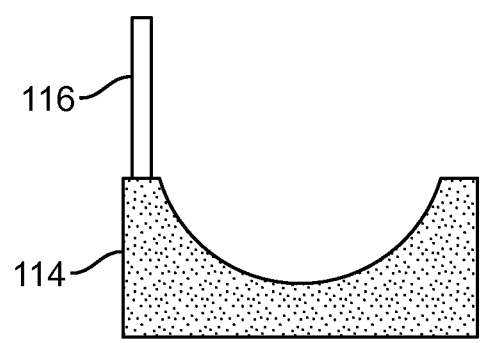
FIG. 10 is a cross-sectional view taken along lines 3-3, depicting apparatus of FIG. 9.

While in a lateral decubitus position, a top leg 106 of the patient 102 is flexed forward at the hip 108 (See FIG. 9). A medial side 110 of the bottom leg 112 is exposed and in full extension. Fluoroscopic imagery is utilized to ensure that the knee is in full extension and in a true lateral position. The operating table may be airplaned and/or moved into slight trendelenberg or reverse trendelenberg to assist in obtaining and maintaining true lateral knee fluoroscopy. Any gap between the medial condyles of the articulating bone structure of the leg is closed by supporting a lateral side of the distal tibia of the bottom leg 112. In this regard, an arch bed 114 can be provided to help properly align the bottom leg 112 (See FIG. 10). The arch bed 114 can further include a post 116 to which interventional tools can be mounted.

The patient and limb can be stabilized with a bean bag or peg board per physician preference. Moreover, the upper leg 106 can be supported by a vacuum lock support 118. The vacuum lock support 118 can be configured to assume a desired shape and subsequently be locked into the desired shape during the interventional procedure. The vacuum lock support 118 structure can also be employed to support other areas of the patient including the lower leg 100 as shown in FIG. 7. Where such structure is utilized, a femoral side of the lower leg 100 should be locked throughout the procedure, whereas the tibial side should be able to be locked and unlocked to allow for rotation. Various angulations of the limbs are necessary during tibial base component fixation and full flexion knee motions must be available.

Figure 11:
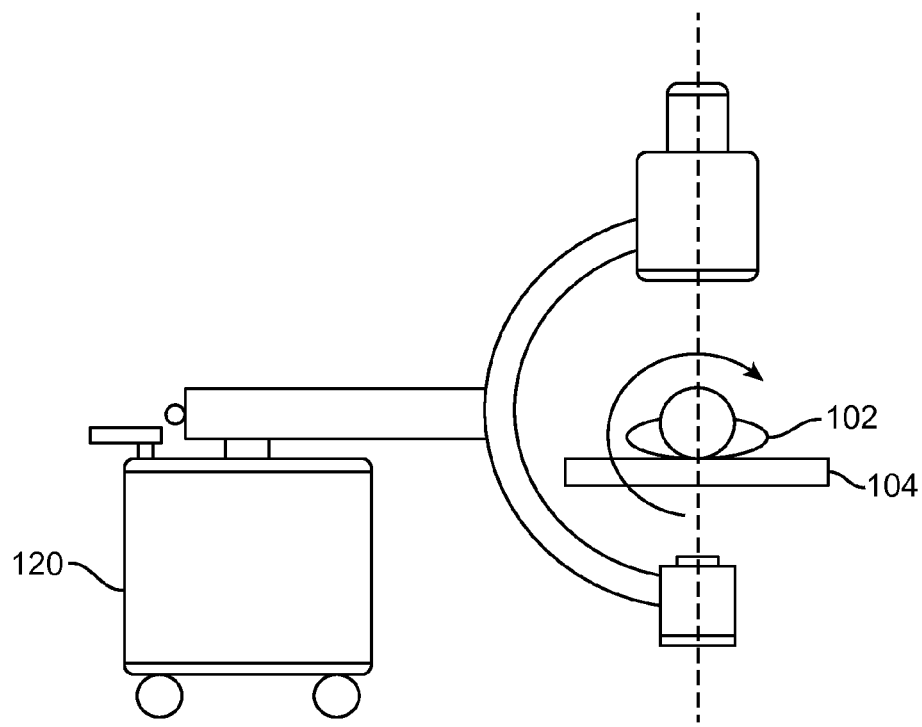
FIG. 11 is a top view, depicting a patient on a surgical platform.
Figure 12:
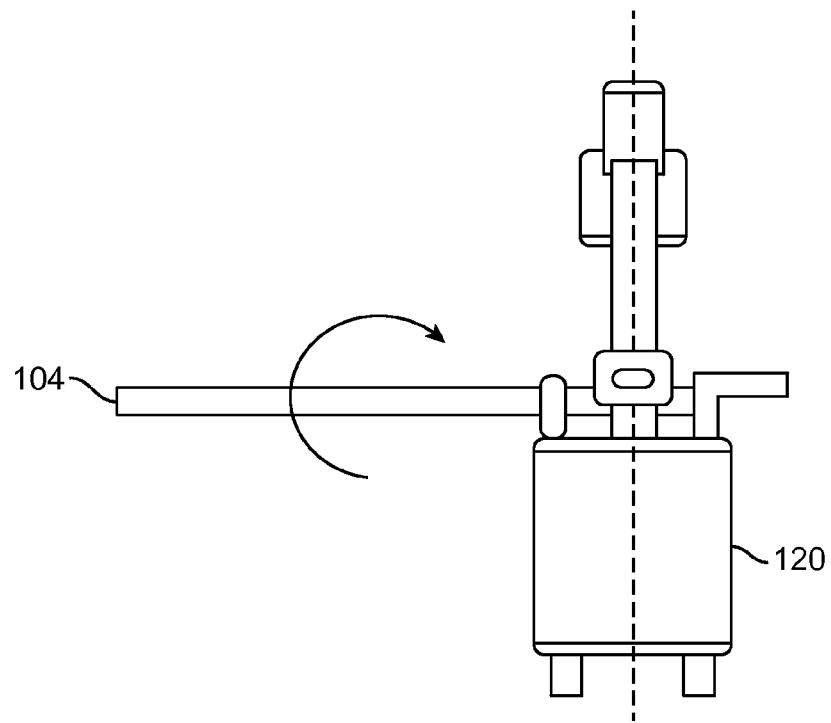
FIG. 12 is a side view, depicting further control of the device shown in FIG. 11.

Once the limbs of the patient are properly positioned, the interventional area is cleaned and shaved as necessary. The entire leg, thigh through foot should be prepared. Under fluoroscopy or other remote imaging means 120, femoral condyles (not shown) are aligned by pivoting the table 104 with table adjustment controls and to again ensure a true lateral view. As shown in FIGS. 11 and 12, the table 104 can be rotated laterally to align posterior condyles and can be rotated longitudinally to align inferior condyles. When necessary, the table 104 can also be rotated along a third axis of rotation to achieve proper leg position-to-remote viewing orientation. Alternatively, the flouroscopy can be rotated to ensure a true lateral view.

During the interventional procedure, the operative articulating knee joint and foot of the patient 102 should be completely exposed and configured outside a drape covering the patient 102. The knee should be free to flex and extend as needed and preferably up to 135° of flexion. Again, any medial condyle gap should be closed by supporting the lateral side of the distal tibia and/or ankle. Once the physician is satisfied with leg positioning and preparation, using palpation to define bone position, tibia and femur base contours are traced onto the skin with a surgical marker.

Figure 13:
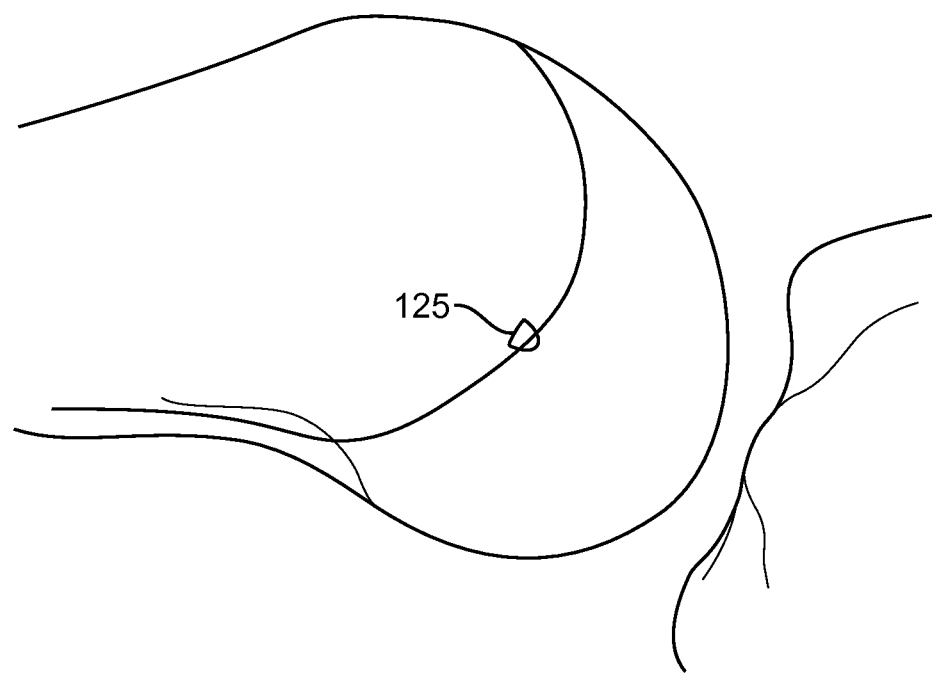
FIG. 13 is a perspective view, depicting a target location on a patient's anatomy.
Figure 14:
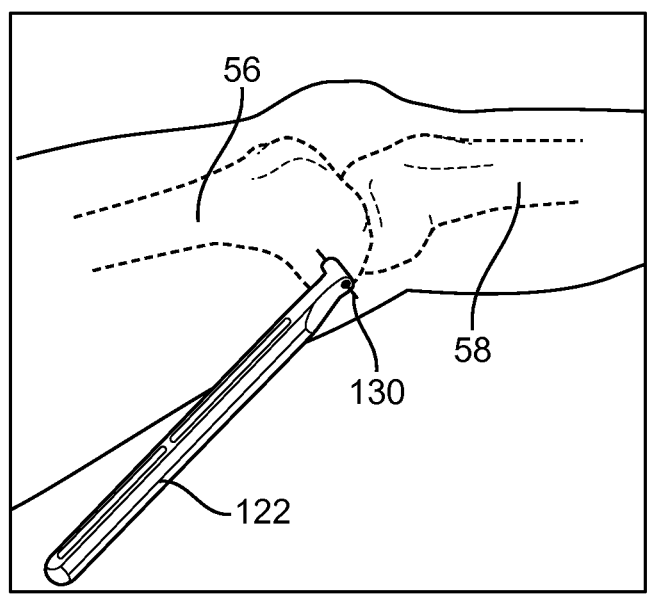
FIG. 14 is a perspective view, depicting one approach for identifying target patient anatomy.
Figure 15:
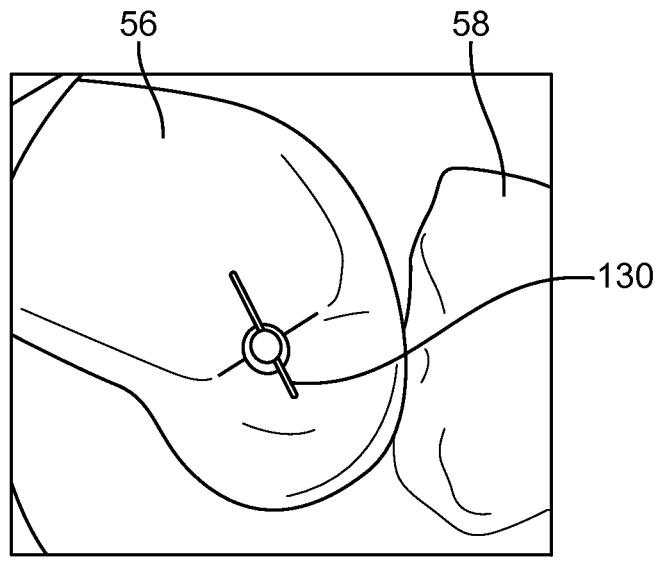
FIG. 15 is an enlarged view, depicting placement of a K-wire into a femur.

In one approach, with reference to FIG. 13, an initial step in treatment involves identifying a patient's Blumensaat's line, which is a structural feature of a femur. Using Blumensaat's line as an anatomical landmark, an acceptable region and target location 125 can be identified for placement of a center of a femoral socket (not shown). With the patient laying on a surgical table as described above with respect to FIG. 1, fluoroscopy or other remote imaging techniques are used to view the anatomy of the lower leg. A bull's-eye tool guide 122 is provided and employed as a guide through which a K-wire 130 is inserted. The tissue in the area is incised minimally posterior and superior to the K-wire 130 held by the tool guide. Next, the K-wire 130 is driven through tissue and into underlying bone at the Blumensaat's line (See FIGS. 14 and 15). It is to be noted that anatomical landmarks (e.g., center of Blumensaat's line, inferior and posterior regions of the femoral condyles) can aid in manually positioning a K-wire in the target location and oriented lateral to the fluoroscopic view using the bulls-eye instrument. So positioning the K-wire aids in subsequently positioning a mechanical energy absorbing structure across a joint. This necessarily involves identifying a center of rotation of the femur. In one approach, the center of rotation is assumed or determined to be at a midpoint of Blumensaat's line.

Figure 16:
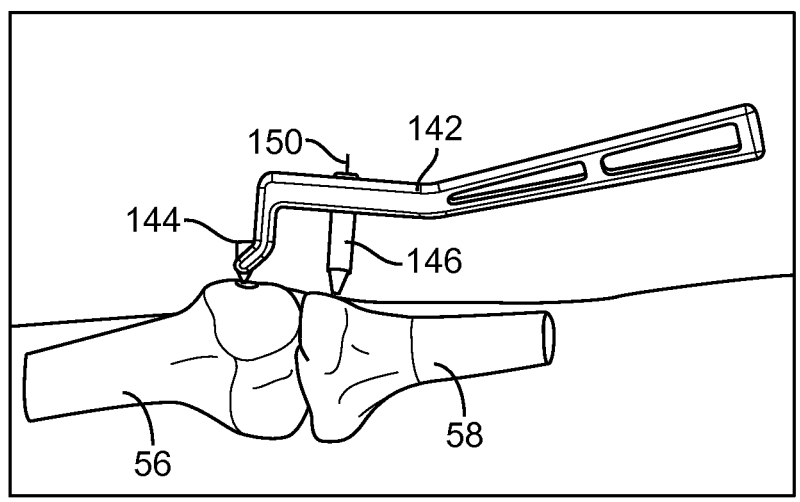
FIG. 16 is a perspective view, depicting use of a tibial guide.

While holding the patient's leg in extension with a varus directed force being applied thereto, a tibial guide 140 is employed to place a temporary tibial K-wire (See FIG. 16). The tibial guide 140 including a handle 142, a distal portion of which is configured with a pivotable femoral point 144. The femoral point includes a central bore sized to receive the K-wire 130 placed in the femur 56. Positioned proximal of the femoral point 144 is a tibial guide member 146 which also include a bore sized to receive a K-wire. The distance between the femoral point 144 and the tibial guide 146 is selected to provide the desired spacing for mounting bases to the bones.

Figure 17:
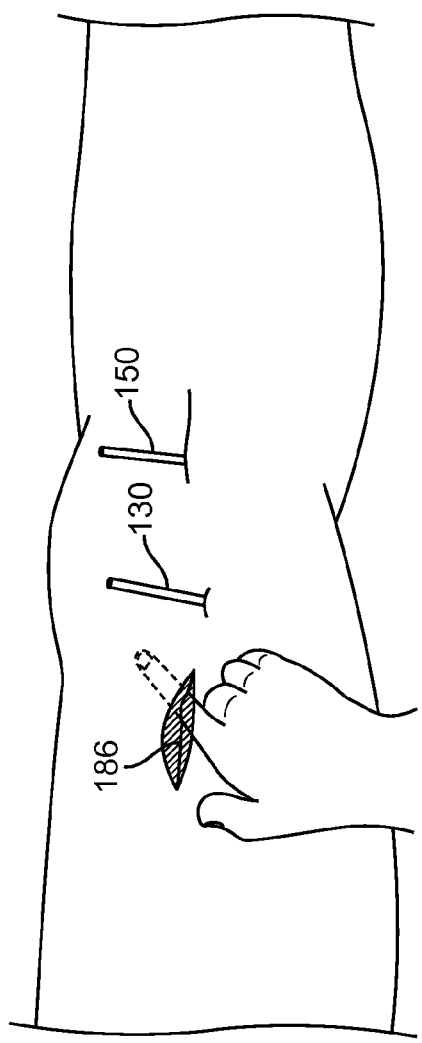
FIG. 17 is a perspective view, depicting physical examination of a mounting site within a patient's anatomy.
Figure 18:
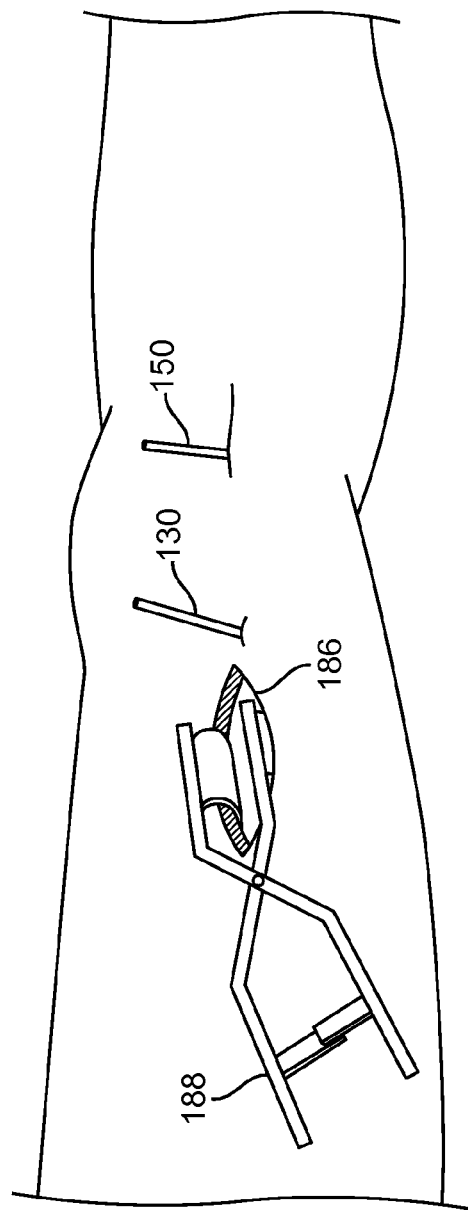
FIG. 18 is a perspective view, depicting use of a refractor and base trial at an interventional site.

With reference to FIGS. 17 and 18, marks (not shown) can be made on a patient's skin to map out a desired component shape and orientation, as well as to identify a location for initial incisions. After making a first incision 186 within the desired area, tissue is dissected to the bone. As shown in FIGS. 17 and 18, in an application to the knee joint, the first incision 186 is made through skin and tissue coincident with the femur. The dissection is made vertically or longitudinally along the leg 175 and is made along natural tissue planes, posterior to the vastus medialus muscle (not shown). The underlying periostium is elevated and removed as necessary while employing standard surgical techniques and an effort is made to avoid disrupting the joint capsule. To prepare the implantation site, access can be provided by a scissor-action refractor 188 at both the femoral and tibial sides of the joint. When possible, the periosteum should be pulled back so that it can be repositioned over the base component once the base has been attached.

Figure 19:
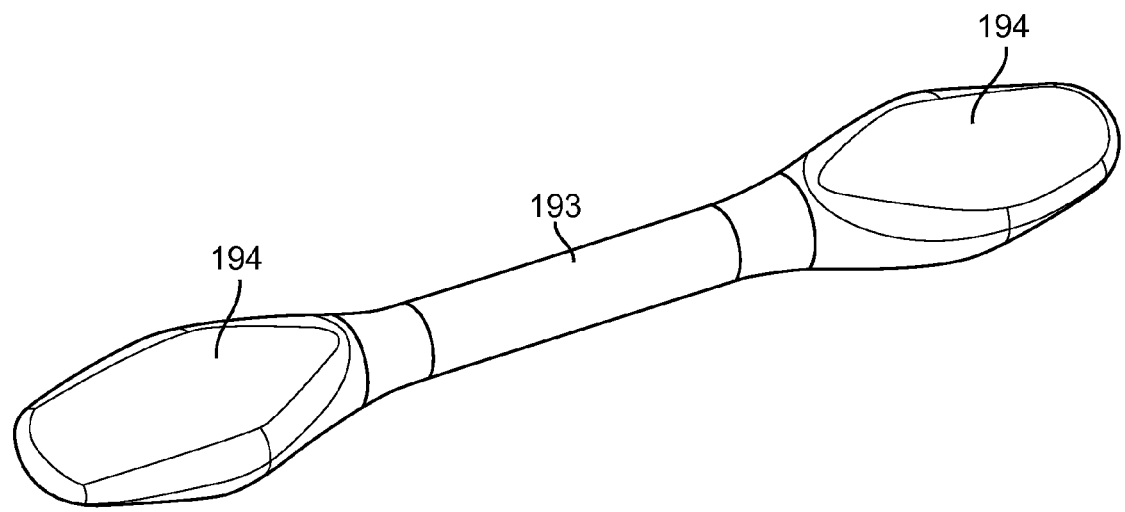
FIG. 19 is a side view, depicting a tunneling device.
Figure 20:
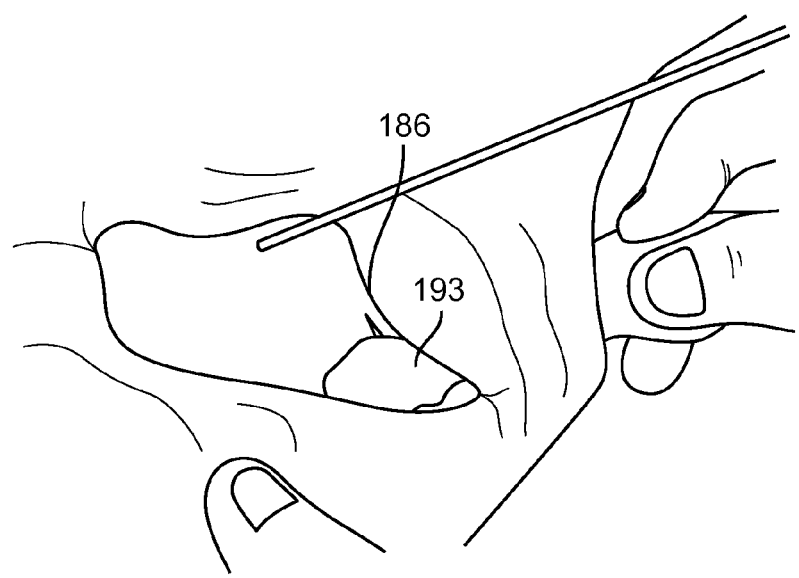
FIG. 20 is a side view, depicting use of the tunneling device of FIG. 17.
Figure 21:
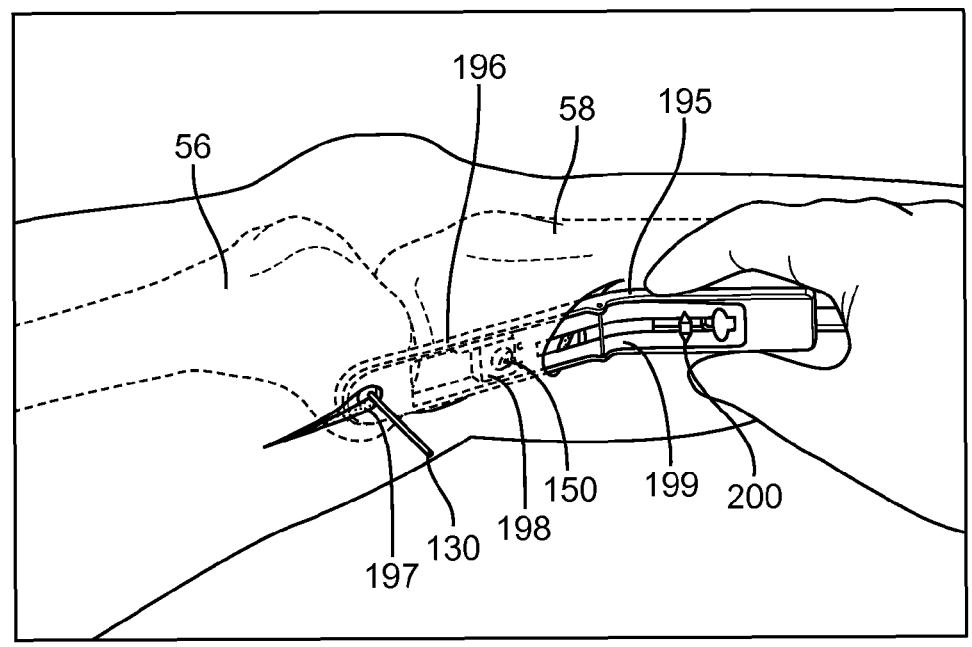
FIG. 21 is a side view, depicting use of a functional test device.

In most instances, an one inch incision on a femoral side of a knee joint is adequate. A tissue dilator or the surgeon's finger can be used for blunt dissection of tissue from the periostium in an area where a base component would be placed and extending to and beyond the point where the K-wire 130 is affixed to bone. The same can be performed in the tibial side of the joint. With reference to FIG. 19, an extracapsular tunnel device 193 a tunnel for an absorber unit is formed beneath the skin and through soft tissue that extends from femoral to tibial incisions. Notably, the tunnel device defines a generally elongate profile and includes paddles 194 at terminal ends thereof. The physician then ensures that the channel is free of fibrous attachments and can accommodate the absorber element. A clear and continuous channel should exist between the expected location for femoral base component and an expected location for a tibial base component. Alternatively, the incision can be extended across the entire length to avoid tunneling. The energy manipulating system can be pushed or pulled through the tunnel between the two incisions. The energy manipulating system can be temporarily housed in a sheath or a dilating introducer.

A functional test device 195 is next employed to determine whether the positions of the K-wires 130, 150 are located such that an energy absorber placed at the site will function as desired. In particular, the test device 195 verifies that length changes of an energy absorber placed at the guide is within acceptable limits. The test device 195 includes a femoral body 196 configured with a femoral guide ball 197 sized to receive the K-wire 130 placed in the femur 56. The device 195 also includes a tibial body 198 attached to a ribbon 199, each of which are slideable with respect to the femoral body 196. It is contemplated that the ribbon 199 includes markings (not shown) corresponding to a permissible range of relative distance between the femur and tibia as these bones articulate. Also attached to the femoral body 196 is a pointer 200 which is configured to remain stationary as the ribbon 199 slides along the femoral body in response to the articulation of the femur and tibia. When the K-wires 130, 150 are properly placed, the pointer 200 will remain within certain of the markings formed on the ribbon 199. Here, the considerations include proper spacing such that the energy absorber will function properly such as without disengagement of parts. To perform the functional test, the pointer 200 is zeroed with the joint members in extension and varus. The joint members are then moved through flexion such as deep flexion angles with valgus movement and external rotation of the bones and minimal flexion with varus and internal rotation. Should the pointer 200 fall outside of a pre-determined range, the K-wire positioning can be selected so that desired energy manipulation is possible for the particular patient being treated.

Figure 22:
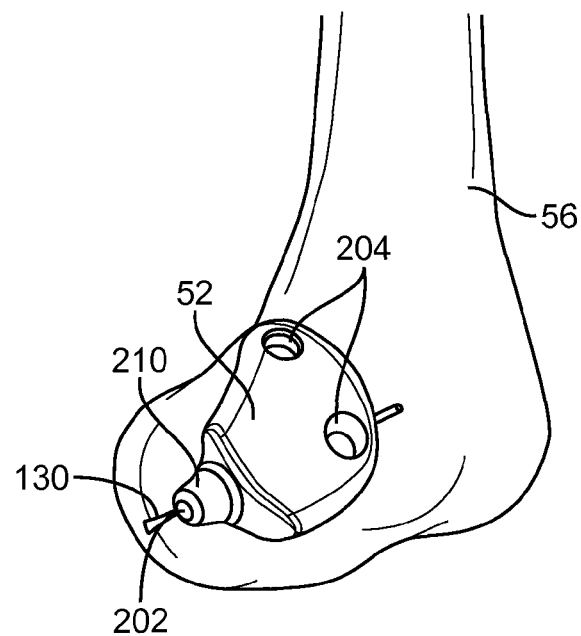
FIG. 22 is a perspective view, depicting a base component placed at an interventional site.

Next, femoral and tibial base components are selected. Once a preferred base component is selected, it is removed from its packaging and visually inspected for any obvious defects. If visual defects are observed another like part is selected. The femoral base component 52 is then placed on the prepared femoral bone 56 by sliding a pivot hole 202 over the femoral K-wire 130 (See FIG. 22). It is to be noted that slight adjustments in position of the base component at this point will assist in seating the base component on the bone and aid finding the best fit between the base component and the bone. Movements should be gently executed to preserve registration of the distal end K-wire location and protect the osteointegration surface.

The femoral base component 56 includes a body having three holes, the pivot hole 202 and two additional holes 204 for receiving fixation screws. As shown in FIGS. 1-6 and 22, the upper surface of the body is a generally curved to provide a surface complementary to the patient's natural anatomy. The base component 56 also includes rounded edges in order to minimize sharp edges that may otherwise cause damage to surrounding tissues when the component is coupled to body anatomy such as the femur. A height or thickness of the base 52 increases from the portion of the base 52 including the two holes 204 to a midsection of the structure at which point there is a ledge and sharp decrease in thickness or height. The curvature of this ledge and thickness of this reduced portion is selected to enable the energy absorbing unit to translate about the pivot hole 202 to a necessary degree such as where members defining the joint form a 140° angle of flexion. It is in this area that is formed a mounting cone 210 which has a profile selected to securely engage a bearing of a socket and bearing assembly of an energy absorber as described below.

According to one embodiment, the holes 204 are threaded and are configured to accept screws that attach the base component onto the bone surface. The screws may be cancellous screws of either uni-cortical or bicortical design. The openings are sized to accommodate a particular screw size.

Additionally, opening 202 is threaded and is provided and positioned such that a fastening member inserted there through will be configured at the center of rotation of the femur. A cannulated screw is contemplated to be placed within the pivot hole 202 so that the same can be inserted about the implanted K-wire 130. In one embodiment, the fastening members can be locking screws and the opening includes threads for engaging like structure of the locking screws. It is to be recognized that locking screws securely anchor the base to the bone such that the relative motion between the base component and the mating bone is less than 150 microns. The locking screws function to stabilize the base component as micro-motions of the base component prevent osteointegration of the base component.

The openings 202, 204 can be oriented to provide fastening member trajectories that maximize pull out forces thereby minimizing the possibility that the base component is separated from the bone. According to one embodiment, the trajectories of the openings are oriented such that the opening trajectories are normal or approximately normal to the shear loading forces on the base component 56. For example, the openings can have differing fastening member trajectories such as the posterior openings 204 orient a fastening member at a downward trajectory, and the anterior opening 204 orients a fastening member at an upward trajectory.

The openings 202, 204 can be countersunk to allow the fastening members to sit below the surface of the base body. In one specific approach, the openings are sized to accommodate 4.0 mm screws. In other approaches, the openings may be sized to accommodate 3.5 mm, 4.5 mm, 5.0 mm, or 6.5 screws.

The inner surface of a base 56 can be roughened or etched surface to improve osteointegration and includes a plurality of feet 230 formed about the holes 202, 204. The feet 220 define the structure which directly engages bone. In this regard, periostium is removed to provide space for the feet. A portion of the interior of the base 52 is separated or spaced from the bone. The inner surface including the feet also can be modified to induce bone growth. Thus, osteointegration can be obtained through mechanical interlocking or as a result of chemical loading. For example, the inner surface may be coated with bone morphogenic protein 2 (BMP-2), hydroxyapatite (HA), titanium, cobalt chrome beads, or any other osteo-generating substance. According to one embodiment, a titanium plasma spray having a thickness of approximately 0.033 in.±0.005 in. is applied to the inner surface. In another embodiment, a HA plasma spray having a thickness of approximately 35 μm±10 μm is applied to facilitate osteointegration.

The base components can be titanium or titanium alloy which promote osteointegration and the wear components can be much harder materials such as cobalt chrome (e.g., Biodur CCM Plus), ceramic, or other durable materials that produce a minimal amount of particulate material or, if particulate material is generated, the smallest size of particulate material.

FIGS. 1A-6 illustrate the base component 52 affixed to the medial surface of the femur. The base component 52 has a generally low-profile when mounted to the bone. The base component 52 is affixed to the medial surface of the femur in order to preserve critical anatomy such as, but not limited to, medial collateral ligaments while positioning the second end of the base component at the center of rotation of the femur.

Figure 24:
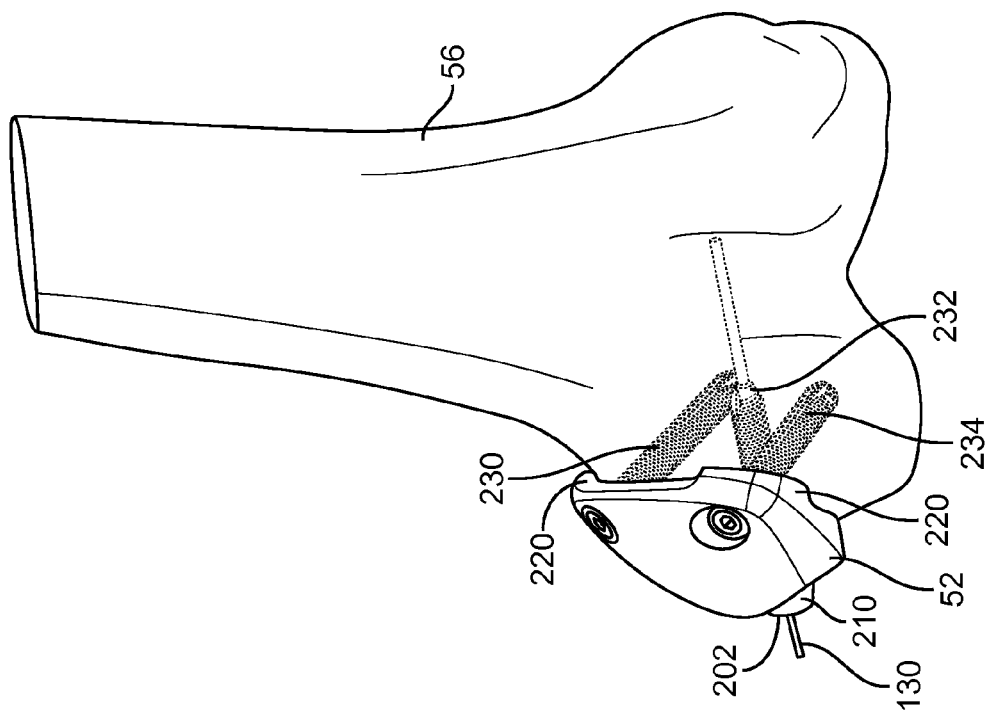
FIG. 24 is a perspective view, depicting attachment of a femoral base to bone.
Figure 23:
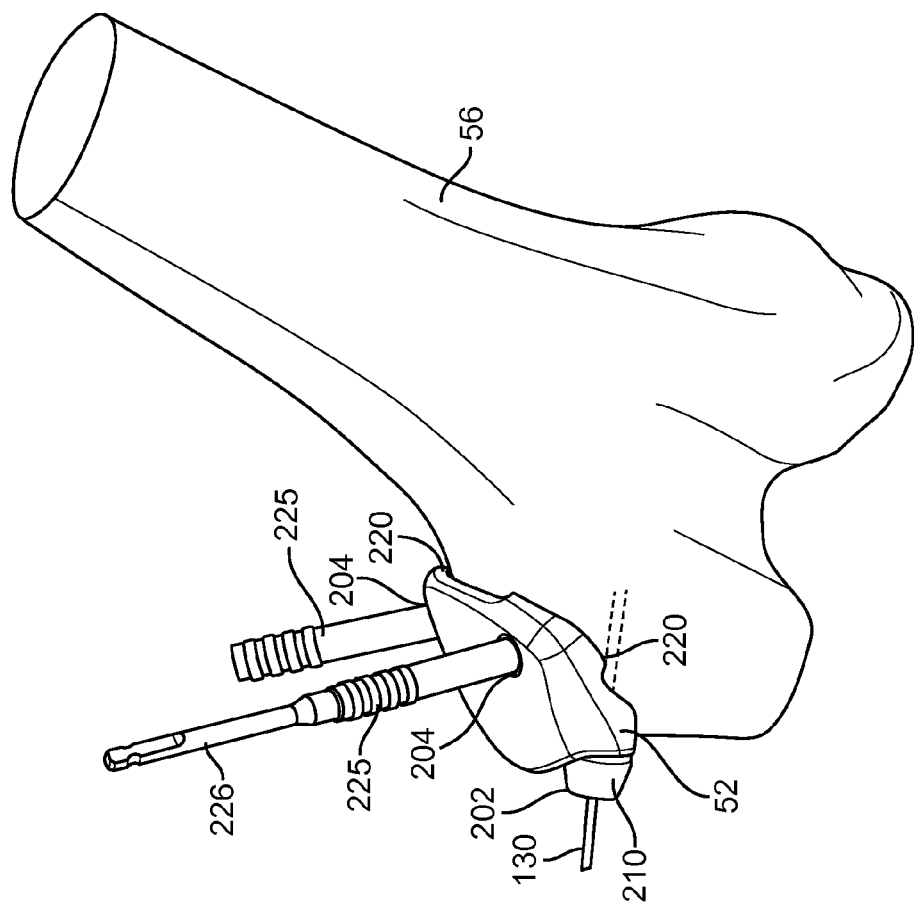
FIG. 23 is a perspective view, depicting use of a drill guide at the interventional site.

Turning now to FIGS. 23 and 24, the fixation of the base components to bone can begin starting with the most superior hole 204. An appropriate drill bit 225 and drill guide 226 are selected. The drill guide 226 has external threads sized to be received by the threads formed in the holes 202, 204, the holes defining the proper trajectory for drilling. The drill bit 225 can then be inserted in the drill guides 226 and the holes can be formed for receiving fasteners. Then screw length is determined by measuring drill holes with a depth gauge in standard fashion.

The pivot hole 202 of the femoral base 52 is first placed over a cannulated plug (not shown) positioned within the guide wire 130. This arrangement facilitates maintaining K-wire trajectory within acceptable limits. The femoral base 52 is then oriented optimally on the femur 56. This orientation can be secured by drilling a K-wire through the inferior of holes 204. Next, the foot 220 associated with the most superior of the holes 204 is attached to bone first by attaching the drill guide 225 to the base 52 and then drilling the bone hole with a drill 226 having a depth stop indicator (See FIG. 23). A screw 232 is then employed to fix this portion of the base 52. The foot 220 associated with the pivot hole is then similarly fixed to the femur 56 by using the locking drill guide 225 and drill 226, and then employing a second screw 232. This second screw 232 is cannulated so as to be placed over the K-wire. Finally, the third foot 220 associated with the third hole 204 is fixed by a third screw 234 once the bone hole is created. The K-wires and drilling aids are removed from the site. As stated, varying trajectory of the screws 230, 232, 234 can be provided to ensure a strong attachment to bone (See FIG. 24).

Figure 25:
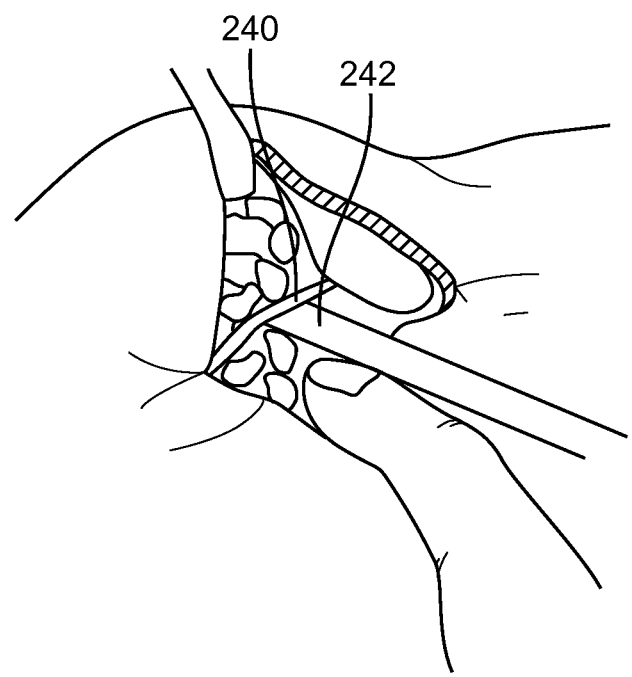
FIG. 25 is a perspective view, depicting forming a space for a tibia base component.

At this time, a tibial base component size can be selected. As shown in FIG. 25, the skin is retracted to provide sufficient bone exposure for placement of the tibial base component. A tibial trial base component can be placed at the side to check the fit (continuous apposition of base to bone is desired around edges). Excessive force of placement should be avoided to preserve integrity of the mounting location. Using sizing templates, the preferred base component can be selected. Sizing should be confirmed to ensure that a majority of the base component edge is secured against the bone with an acceptable minimum distance in any gap areas. The periostium 240 is removed in contacting regions of the tibial base using a blade, curette or periosteal elevator 242. A sufficient region of periosteum should be removed or retracted to provide intimate contact between the entire base component surface and bone. It is to be recognized that inadequate removal of periosteum may prevent osteointegration of the bone into the base component. Moreover, excessive removal of periosteum beyond the base component margins may reduce blood supply to the bone. When possible, the periostium should be pulled back so that it can be repositioned over the base component once the base has been attached.

Once a proper sized tibial base is selected, it is removed from its packaging and visually inspected for any obvious defects. If visual defects are observed, another component is selected.

Figure 26:
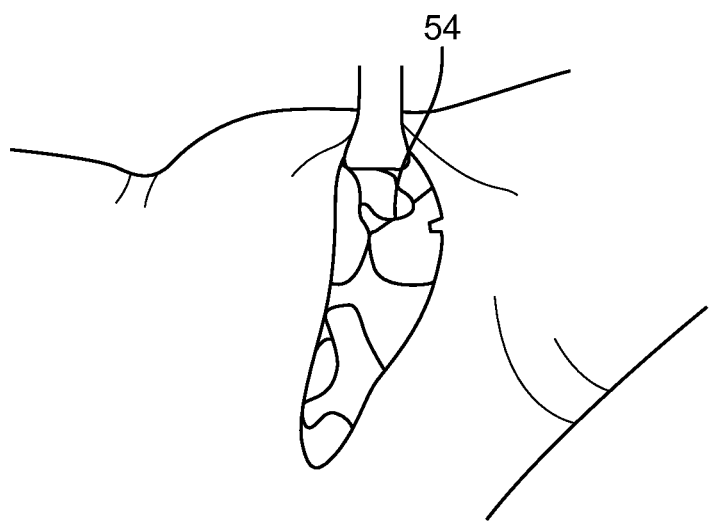
FIG. 26 is a perspective view, depicting attaching a tibia base to an absorber.

As shown in FIG. 26, the tibial base component 54 is then placed onto the prepared tibial bone and it is readjusted to find the optimal positioning. During tibial attachment, the knee should be in full extension with varus stress for a medial placement. In certain applications as for example those relating to knee, it has been found to be beneficial to close a gap between the bones forming a joint and then selecting an optimum position for placement of the second base component. Further, varus or valgus stresses can be applied to close the gap between the joint members. In this way, the ultimate positioning of the second (tibial) base will then involve ensuring that there will be sufficient space between joint members when a complete extra-articular mechanical energy absorbing apparatus is placed across the joint. Moreover, slight adjustments in position of the tibial base component 54 at this point will assist in seating the base component on the bone and aid in finding the best fit between the base component and the bone. Adjustments in base position should be gently executed to protect the osteointegration surface on the base component.

Figure 27:
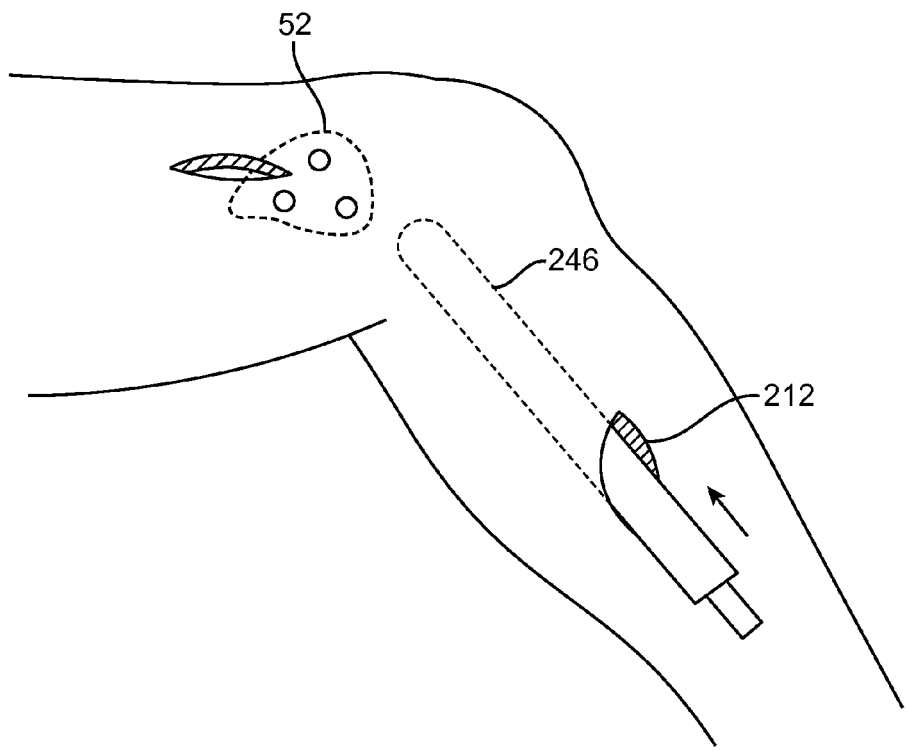
FIG. 27 is a perspective view, depicting inserting an absorber tool attached to a tibial base at an interventional site.
Figure 28:
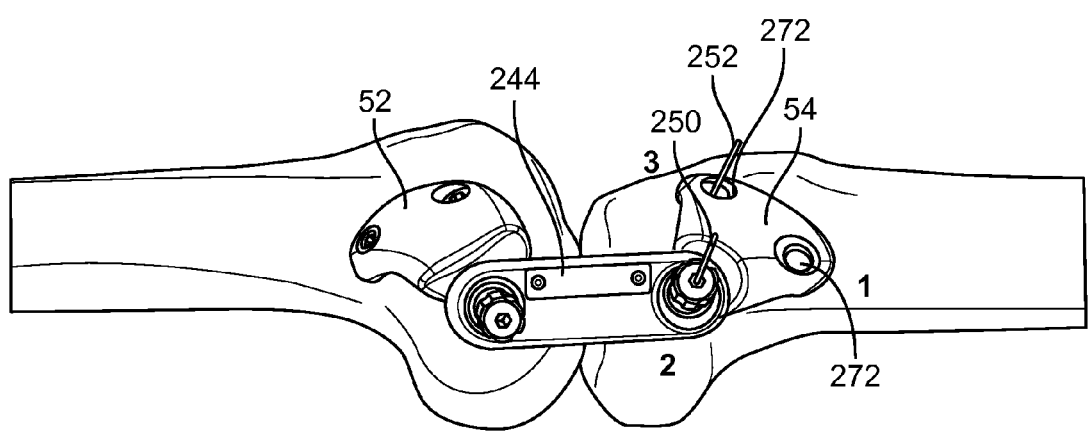
FIG. 28 is a perspective view, depicting placement of the absorber tool to a first base.

A dummy absorber 244 and a tibial base 54 are then connected and the assembly is advanced under the skin towards the first base 52 (See FIGS. 27 and 28). Whether using the dummy link or the fixed distance link, steps are taken to connect the same to the first base 52 (See FIG. 28). In this regard, an insertion tool 246 can where desirable, be employed to advance the dummy absorber and attached tibial base 54 through the implantation site. The dummy absorber 244 is then attached to the implanted femoral base 52 and the pivot point for the tibial base 54 is identified. While holding the incision 212 open, screws or other fasteners are used to fix the second base component to the bone. Verification of placement is confirmed through remote imaging.

Figure 29:
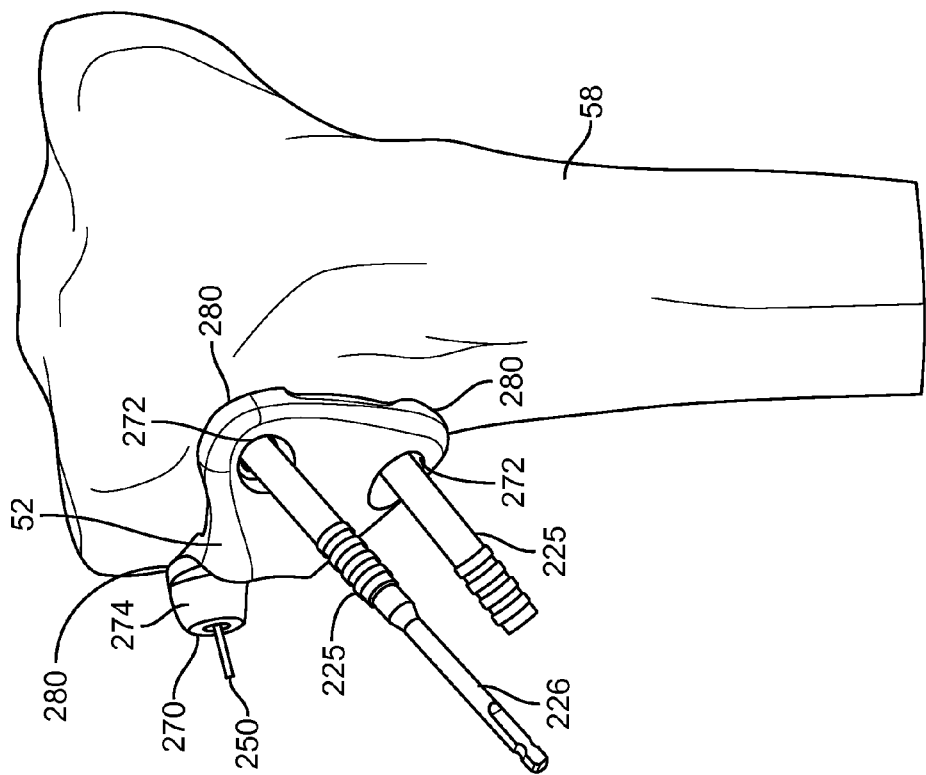
FIG. 29 is a perspective view, depicting use of a guide in combination with a second base at an interventional site.

It is to be recognized that a presently preferred embodiment of base component 54 is mountable to the medial surface of the tibia is depicted in FIGS. 1A-6. As shown, the tibial base component 54 has an overall curved shape and a body having three holes, a patient hole 270 and two additional holes for receiving fixation screws (See FIGS. 28 and 29). The upper surface of the body is a curved convexly to provide a surface complementary to the patient's anatomy.

A height or thickness of the base 54 increases from the portion of the base 54 including the two holes 204 to a midsection of the structure at which point there is a ledge and sharp decrease in thickness or height. The curvature of this ledge and thickness of this reduced portion is selected to enable the energy absorbing unit to translate about a pivot hole 270 to a necessary degree such as where members defining the joint form a 140° angle of flexion. It is in this area that is formed a mounting cone 274 which has a profile selected to securely engage a bearing of a socket and bearing assembly of an energy absorber as described below. The base component 54 also includes rounded edges in order to minimize sharp edges that may otherwise cause damage to surrounding tissues when the component is coupled to the tibia.

Additionally, the openings 270, 272 are oriented to provide differing trajectories for fastening members that maximize pull forces thereby minimizing the possibility that the tibial base 54 component is separated from the bone. According to one embodiment, the opening trajectories are oriented such that the hole trajectories are normal or approximately normal to the shear loading forces on the tibial base component 54.

As before, the openings 270, 272 can be countersunk to allow the heads of fastening members to sit below the surface of the body of the base. According to one embodiment, the openings are sized to accommodate 4.0 mm diameter fastening members. In other embodiments, the openings may be sized to accommodate 3.5 mm, 4.5 mm, or 5.0 mm diameter fastening members. Additionally, the inner bores of the openings may be threaded for use with locking screws (i.e., head of the screw also includes threads that engage threads in the bore of the screw hole).

In one affixation approach, while applying varus stress with the joint members in extension, the tibial pivot point is selected at that point directly inferior to the femoral pivot point. A K-wire 250 is then driven through the tibial pivot point (identified as 270 in FIG. 29). The tibial base 54 is next optimally oriented on the bone. Orientation is secured by driving another K-wire 252 through a cannulated plug (not shown) placed in the hole 272 just superior to the most inferior hole 272.

While screws are used to fix the tibial base component 54 to the bone, those skilled in the art will appreciate that any fastening members known or developed in the art may be used to accomplish desired affixation. Although the base component 54 depicted in the FIGS. illustrate structure having three openings, it is contemplated that other embodiments of the base component may be have any number of openings. Additionally, the openings may be oriented such that fastening members will have different trajectories.

The inner surface of the tibial base can be a roughened surface for improving osteointegration and includes a plurality of feet 280 formed about holes 270, 272. The feet 280 define the structure which directly engages the bone. A portion of the interior of the base 54 is separated or spaced from the bone. Alternatively or additionally, the inner surface including the feet 280 is coated to induce bone growth. For example, the inner surface may be coated with bone morphogenic protein 2 (BMP-2) or hydroxyapatite, titanium, cobalt chrome beads. The inner surface can include a contoured surface that promotes good contact between the base component 54 and the tibia. Accordingly, the inner surface facilitates the base component 54 absorbing and transferring load forces from the base component to the tibia.

Figure 30:
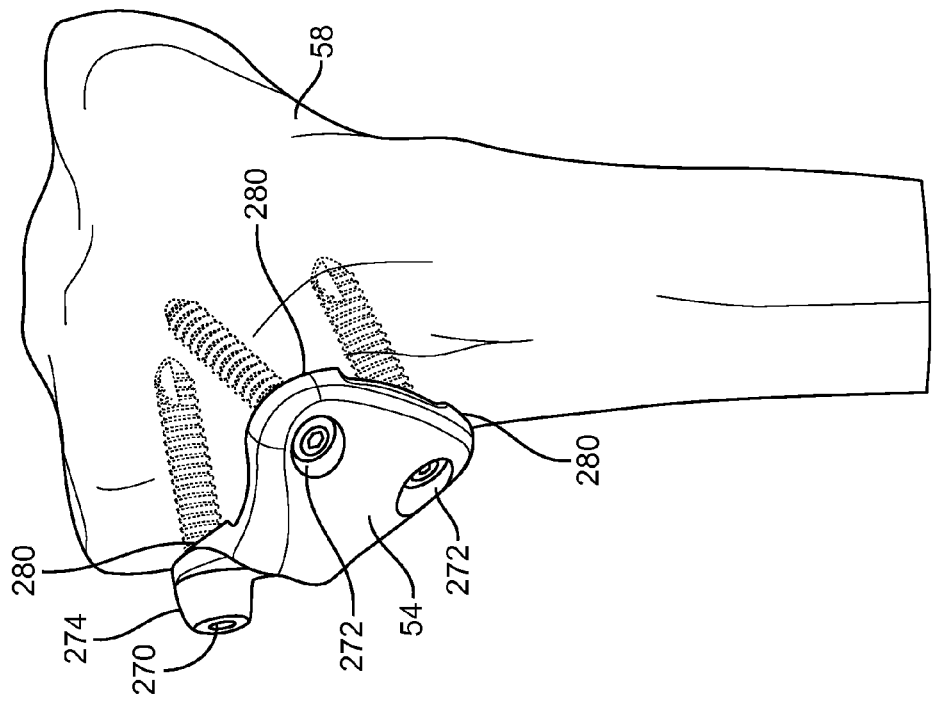
FIG. 30 is a perspective view, depicting an implanted second base.

Referring again to FIG. 29, the foot 280 associated with the most inferior positioned of the non-pivot holes, namely hole 272, is attached to the tibia. As before, a drill guide 225 is screwed into place within this hole 272 and the drill 226 is employed to form a hole in bone. A fixation screw is then employed to fix the first foot 280 to the tibia. Next, the foot 280 associated with the pivot hole 270 is attached to the tibia 58 again first by forming a hole in the bone using the drill guide 225 and drill 226. A cannulated screw is employed to attach this foot so that fixation can be accomplished over the K-wire. The dummy absorber 244 (shown in FIG. 28) is then removed from the site. Finally, the third foot 280 is similarly attached to the tibia 58 first by drilling a hole and then using screws. FIG. 30 depicts a tibial base 54 attached to a tibia. FIG. 30 depicts a tibial base 54 attached to a tibia. The various employed K-wires can then be removed from the site.

The tibial base component 54 has a generally low-profile when mounted to the bone. The base component 54 is mounted to the medial surface of the tibia in order to preserve critical anatomy such as, but not limited to, medial collateral ligaments.

The base components 52, 54 are configured to be fixed to the medial surface of the left femur and tibia. As those skilled in the art will appreciate, a mirror image of the base components would be fixable to the medial surface of the right femur and tibia. Additionally, the base components may be configured to be fixed to the lateral surface of the left or right femur and tibia. In another approach, the base component may be configured to be coupled to lateral surfaces of both the femur and tibia and fibula. In yet another embodiment, base components may be fixed to both the lateral and medial surfaces of these bones.

Figure 31:
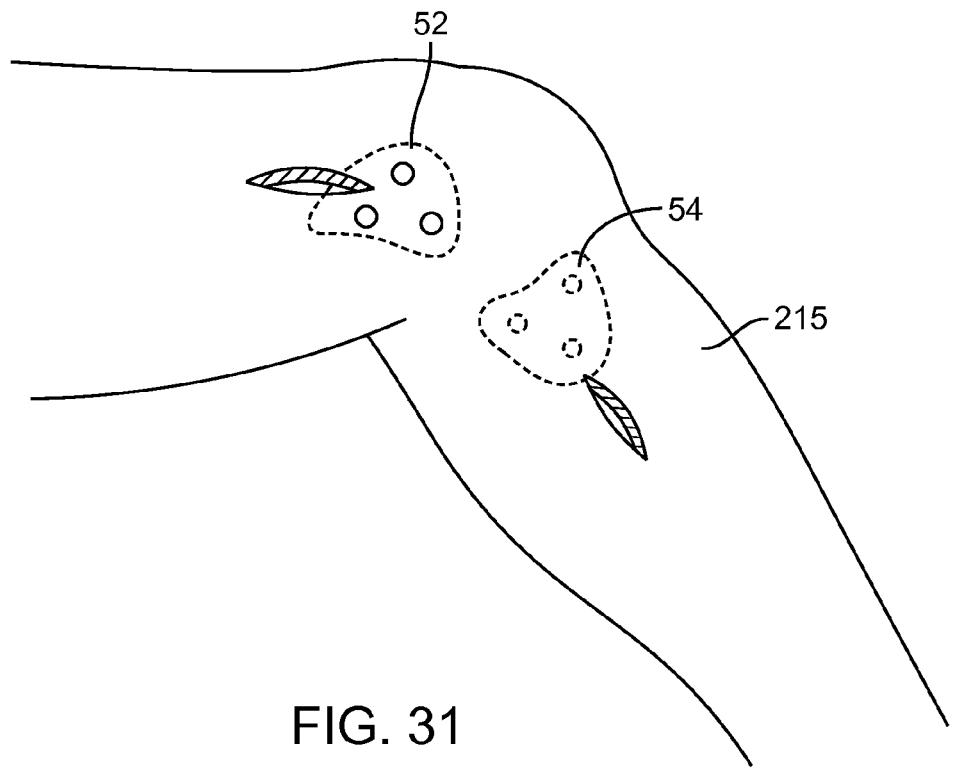
FIG. 31 is a partial cross-sectional view, depicting removal of a dummy link from the interventional site.

As shown in FIG. 31, after removing structure maintaining the position of the leg in an extended position, the lower portion of the leg is flexed so that it forms an angle with the upper leg. Thereafter, a desired energy absorbing assembly is placed at the interventional site. An insertion tool 300 such that schematically depicted in FIG. 32 can be employed to place the desired energy absorbing device to span the implanted bases 52, 54. It is contemplated that such an energy absorbing device be covered with a sheath 61 (See FIG. 1A).

Figure 34:
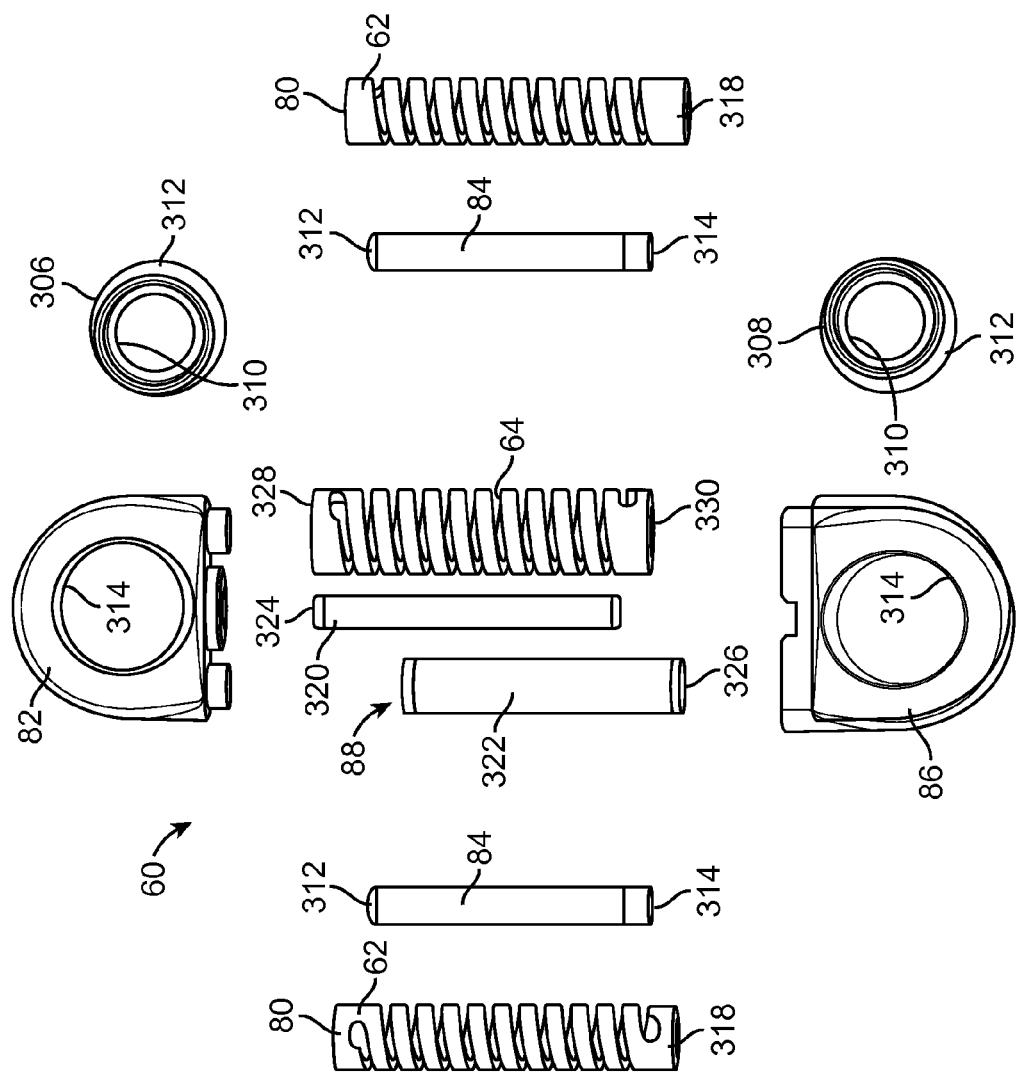
FIG. 34 is an exploded view, depicting the absorber assembly of FIG. 33.
Figure 33:
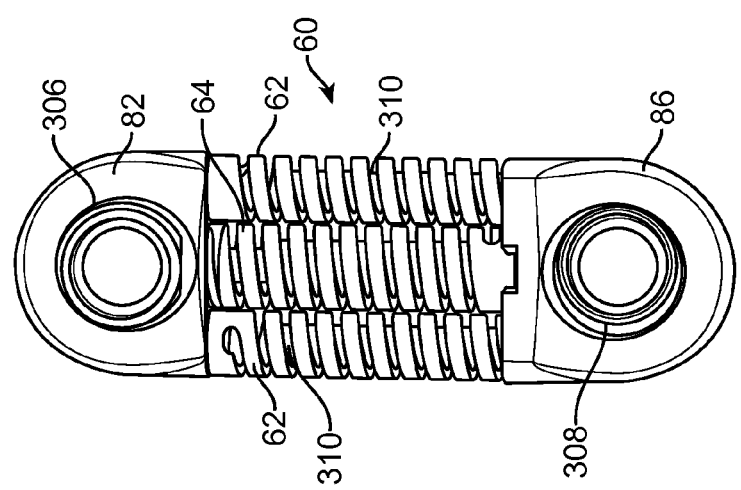
FIG. 33 is a top view, depicting an absorber assembly.

Turning now to FIGS. 33 and 34, features of the energy absorber 60 are now described. The configuration of the springs may be varied to minimize device size while maximizing its energy absorbing capabilities. Moreover, various types of springs such as coaxial or leaf springs can be employed and the spring structure can be placed serially and adjusted one by one. The springs could also be substituted with a material or other device with spring-like characteristics (e.g., an elastomeric member). Such elastomers include thermoplastic polyurethanes such as Tecoflex, Tecothane, Tecoplast, Carbothene, Chronthane and Chrono-Flex (grades AR, C, AL) which also could be employed as a dampener. Moreover, materials such as Pebax, C-flex, Pellathane and silicone and silicone foam can also be employed.

As stated, an extra-articular implantable mechanical energy absorbing system 60 is coupled to the femoral and tibial base components 52, 54, respectively. The components of the absorber 60 are sized and configured so that sliding and articulating members remain in tact and assembled while members of the joint to which the components are attached move through the full anticipated angles of motion. Through the connections provided by the base components 52, 54, the mechanical energy absorbing system 60 can function to reduce desired forces from a knee joint. It is also to be recognized that the placement of the bases on the bones is made such that further procedures, such as a TKA, can be conducted at the joint while leaving the bases in place but after removing the absorbing system. Additionally, the absorbing system can be replaced without having to replace the base components resulting in removal of all of the wear components. To connect the absorber 60 to the bases 52, 54, structure is employed to attach a first end of the absorber 60 to the femoral base 52 and a second end of the absorber 60 to the tibial base 54.

Referring now specifically to FIG. 34, the absorber includes a pair of sockets 82, 86 each of which are sized to pivotably receive a spherical bearing 306, 308. These bearings include an inner annulus 310 that is configured to be press fit with the cone structure 210, 274 (See also FIGS. 29 and 30) formed on the bases 52, 54. Required inter-positional spacing relationships between the sockets are insured by the sizing of the base cones 210, 274 and the energy absorber 60 such that full mobility of the members defining the knee joint is not impeded. As stated previously, the energy absorber 60 pivots with respect to the bases 52, 54 and within the narrowed thickness area of the bases provided about pivot points.

An outer surface 312 of the bearings 306 embodies a section of a generally spherical profile. This outer surface 312 is sized and shaped to be retained within an opening 314 formed in the sockets 82, 86. A pair of cutouts (not shown) are provided in the sockets 82, 86 to permit the insertion of the bearing 306, 308 within the sockets 82, 86. In this regard, the bearing 306, 308 can be first turned perpendicular to the socket 82, 86 to accomplish such insertion and then rotated so as to seat the bearing 306, 308 flush with the socket 82, 86.

As previously mentioned, the absorber further includes three springs. In one approach, outside springs 62 have a first diameter and an inside spring 64 has a second larger diameter. The outside springs 62 are each configured about the spring guide pin 84, a first end 312 of which is free floating when the absorber 60 is in an assembled form and a second end 314 which is fixed within a hole (not shown) formed in the bottom socket 86. As best seen in FIGS. 5 and 6, the outer springs include a first end 80 fixed to the top socket 82 about a post and a second end 318 which engages the bottom socket 86 when the limbs of the joint are in extension thereby accomplishing a desired energy manipulation. A second end 318 of the springs 62 is floating providing no energy manipulation function when the limbs approach and are in flexion.

The larger middle spring 64 is configured about the piston and tube arrangement 88 which consists of a piston 320 which is slideable within a tube 322. Here, the piston 320 includes a first end 324 which is fixed within a hole formed in the top socket 82 and the tube includes a first end 326 fixed within a recess formed in the lower socket 86. Also, a first end 328 of the middle spring 64 is free floating and a second end 330 is fixed to the lower socket 314. When the limbs of the joint are in extension (FIG. 1B) the middle spring 64 accomplishes desired energy manipulation and when the limbs approach and are in flexion (FIG. 6), the free end 328 of the spring 64 provides no energy manipulation.

Figure 32:
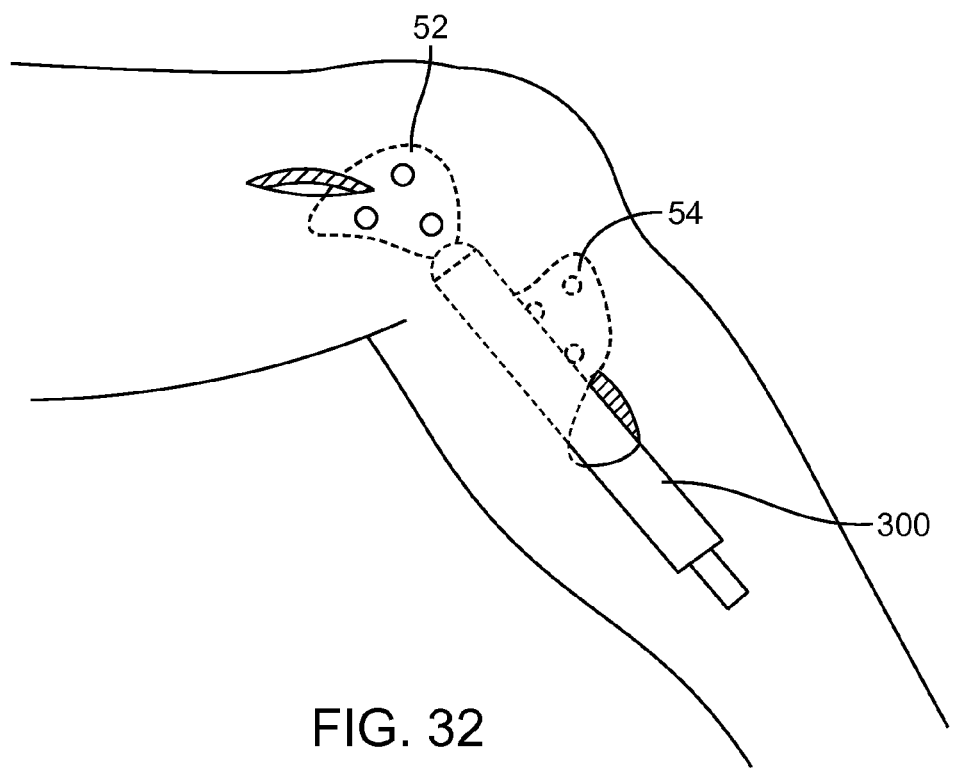
FIG. 32 is a partial cross-sectional view, depicting use of guide tube to insert an absorber assembly site.
Figure 35A:
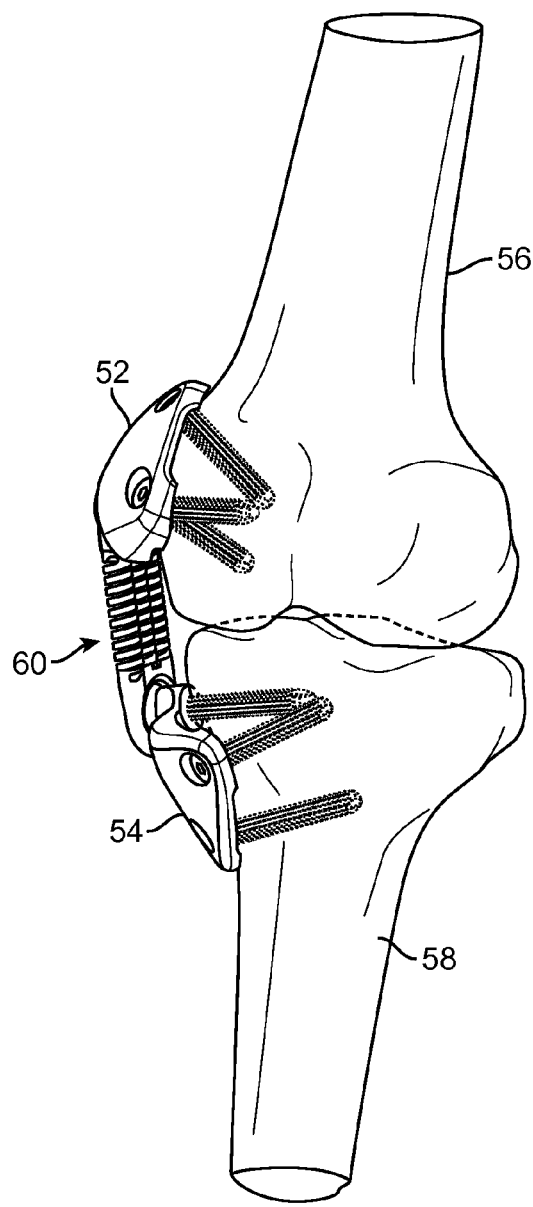
FIG. 35A is a perspective view, depicting an implanted energy manipulation system.
Figure 35B:
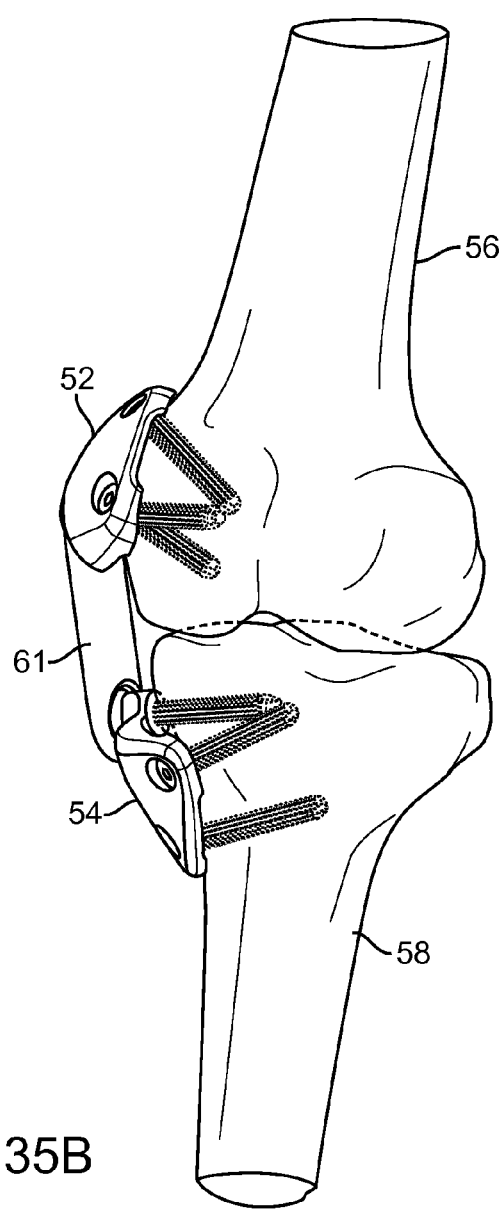
FIG. 35B is a perspective view, depicting the system of FIG. 35A with the sheath in place.
Figure 39:
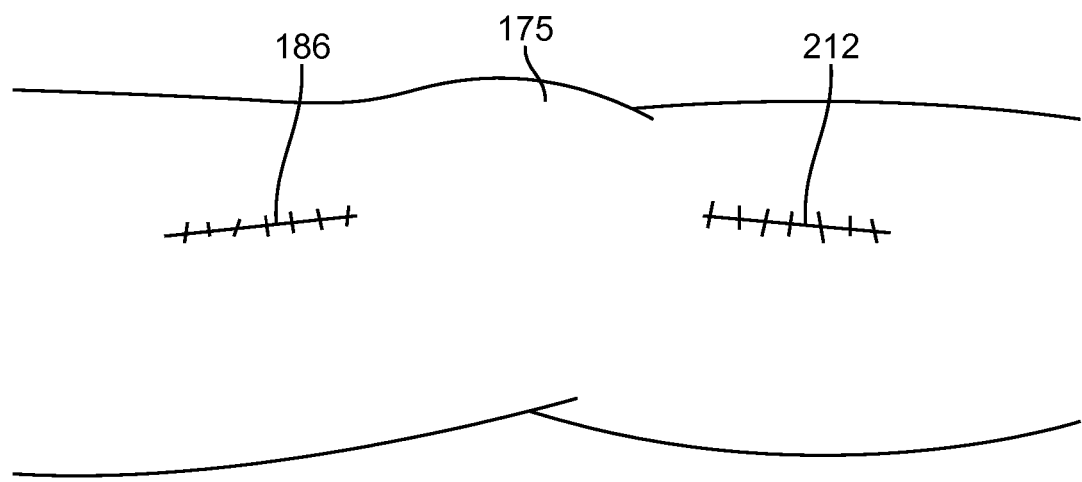
FIG. 39 is a perspective view, depicting an exterior of body anatomy having mechanical energy absorbing apparatus implanted therein.

After inserting the energy absorber within the interventional site as shown in FIG. 32, with the joint members flexed, the sockets 82, 84 are each placed about one cone structure 210 of the bases 52, 54. Bearing screws 340 (See FIG. 1A) are then used to fix the absorber 60 in place. A break-away torque driver can be used here to ensure proper tightening while avoiding over torquing. FIGS. 35A and B depict an absorber affixed a knee joint, the latter figure including a depiction of the sheath 61.

Various aspects of the sheath are illustrated in FIGS. 36-38E. According to one embodiment, the sheath 61 is an elongated tube having an inner passage or space extending the length of the elongated tube. The sheath includes an attachment mechanism for securing the sheath about the absorber 60. In one embodiment, the sheath promotes the formation of a fibrous capsule around the implanted system thereby isolating the device from surrounding body structure. Alternatively, the sheath includes (or is made from) material that promotes tissue ingrowth. In either embodiment, the sheath isolates the mobile elements of the implanted system from surrounding tissues and prevents tissue adhesions to components of the implanted system. As a result, tissue impingement on the components of the implanted system is minimized thereby facilitating the replacement of the various components of the extra-articular implantable mechanical energy absorbing system.

It has been found that in certain situations, adjustments to an implanted energy absorbing or manipulating system are necessary. In other scenarios, it may be necessary or beneficial to remove the implanted system from the interventional site. Accordingly, the capsule the sheath provides about the implanted system aids in accomplishing adjustments or completed removal of the system. That is, the capsule created by the sheath provides a convenient space for accessing the energy manipulating system contained within the sheath.

In a preferred approach, the sheath 61 is an elongated tube having a first end 350 opposite a second end 352. The sheath 61 includes an inner bore that is sized to envelop rounded absorber 60. The sheath 61 is a generally flattened tube having rounded ends. The sheath generally conforms to the underlying shape of the absorber and protects the implanted system from surrounding tissue. In this way, the implanted energy absorbing system is substantially or completely excluded from tissue ingrowth and can operate unimpeded and as intended. The sheath 61 also provides an outer profile well suited for exhibiting a natural appearance and feel under and through a patient's skin.

Generally, the inner diameter of the sheath is dimensioned off the enveloped energy absorber component such that there is approximately 1 mm of clearance between the sheath and the component.

Additionally, the disclosed sheaths can have an overall length of about 90 mm and may have a uniform wall thickness. According to one embodiment, the sheath 61 has a wall thickness of approximately 0.6 mm throughout the entire length of the sheath. In other embodiments, the sheath has a wall thickness ranging from approximately 0.5 mm to 1.0 mm. In yet another embodiment, the sheath has areas of variable thickness. The thickness of the wall is varied based upon the wear requirements, the desired cosmesis effect, and location of use within the body.

The medial side 356 of the sheath 61 is shown in FIG. 36. In one approach, a distance between center points of holes 358 formed in the medial side is approximately 60 mm. The holes 358 are centered, reinforced such as with a 12 mm diameter button 360 with a 9 or 10 mm access port. The buttons 360 are fixed to an inside of the sheath 61 and present a smooth exterior. The buttons 360 are approximately 1 mm thick.

The lateral side 362 (See FIG. 37) also embodies a pair of holes 362 also spaced approximately 60 mm. These holes 362 are also reinforced with buttons 364 but here the buttons 364 have a 16 mm diameter with an about 12 mm access port. The buttons 364 again are affixed to an inside of the sheath, have a thickness of about 1 mm and present a smooth exterior surface.

The disclosed sheaths shown in the previous figures as well as those described below may be made from different materials depending on the desired physical properties. For example, the outer surface may be composed of materials to promote or inhibit tissue ingrowth. Optionally, the outer surface of the sheath may be coated, impregnated, or otherwise includes one or more drugs and/or compositions that promote or inhibit tissue ingrowth around the sheath. Materials designed to promote tissue ingrowth include, but are not limited to, Polyester velour fabric manufactured by Bard (e.g., Part Numbers 6107 and 6108) or a polypropylene mesh. It is noted that ePTFE of different pore sizes can induce ingrowth. Tissue ingrowth into the sheath provides a tissue capsule in which the implanted system is secured within. The capsule protects surrounding tissue from possible damage from the implanted system as well as preventing tissue impingement upon the components of the implanted system. Additionally, the capsule allows the components and parts of the implant system to be easily accessed for maintenance and/or service since the components are located within the fibrous capsule. If a sheath is configured to include tissue ingrowth, then tissue is attached to the sheath with the benefit being no relative motion between the implant and tissue. Thus, all relative motion is between the moving implant and inner diameter of the sheath.

Materials that inhibit tissue ingrowth include, but are not limited to, expanded polytetrafluoroethylene (ePTFE) supplied by Zeus or International Polymer Engineering, polytetrafluoroethylene (PTFE) supplied by Bard (e.g., Bard p/n 3109, 3112, or 6108), polyetheretherketone (PEEK) supplied by Secant Medical, silicone supplied by Accusil, Limteck, Promed Molded Products, Silicone Speciality Fabricators, TYGON® (e.g., 80 shore A material), or thermoplastic polymers such as, but not limited to, C-FLEX®. Sheath embodiments made from one or more of the above-listed materials encourage tissue surrounding the sheath to form a non-adherent pseudo-capsule around the sheath. The pseudo-capsule isolates and stabilizes the implanted system thereby allowing easy access to the system while preventing tissue impingement upon the components of the implanted system.

In those sheath embodiments formed from ePTFE, the length change of the link or absorber element of the implanted system due to the flexion of the members to which it is attached, is taken up by the sheath material. It has been discovered that ePTFE is a preferred material for the sheath because it has good flexing and bending characteristics without kinking, it accommodates twisting, lengthening and shortening and it is a soft material that presents a soft surface to the surrounding tissues. Expanded PTFE has a microstructure having roughly parallel-running clumps of material (i.e., nodes) with perpendicular fibers (i.e., fibrils) connecting the nodes together. The spacing between the nodes and the fibrils of the ePTFE sheath allows for significant elongation and compression of the material (via stretching and compression of the fibrils) without adverse impact on the shape (e.g., inner or outer diameter) of the sheath. Additionally, the ability of the sheath to contract and expand allows the sheath to place a low tensile/compressive load on the moving link or absorber element of the implanted system.

According to one embodiment, a sheath made from ePTFE has an internodal distance of 25 microns. The low internodal distance has increased lubricity and radial strength as compared to materials having a high internodal distance. The low internodal distance of the material limits tissue ingrowth into the outer diameter of the sheath. In an alternate embodiment, the ePTFE has an internodal distance of 50 microns. The high internodal distance has decreased lubricity and increase porosity as compared to material having a low internodal distance. The high internodal distance has more tissue ingrowth (e.g., tissue penetrates wall). In yet another embodiment, one embodiment of a sheath includes a main body having a low internodal distance (e.g., 25 microns) that covers the absorber elements of the system, and end portions having a high internodal distance (e.g., 50 microns) that covers the base components.

According to one embodiment, the outer surface is made from a single type of material. In other embodiments, the outer surface is made from a plurality of materials. For example, the main body of the sheath is made of ePTFE, and the ends of sheath are made of PTFE. In this embodiment, the PTFE ends may be sutured to the ePTFE main body. Alternatively, the PTFE ends may be fused (or sintered) with the ePTFE main body.

Alternatively, the various embodiments of the sheath can be composed of a plurality of layers. In one embodiment, the sheath includes an outer layer that promotes or inhibits tissue ingrowth and one or more inner layers. The inner layer may be composed of a silicone sleeve, silicone foam layer, or a hydrogel. The silicone layer is used for padding in some embodiments. In another embodiment, the ends of the silicone layer are shaped to provide better fit of the sheath onto the base component. In another embodiment, the sheath includes an outer layer, a middle layer composed of a silicone layer, and an inner layer composed of ePTFE or PTFE. The inner layer may be coated with a lubricious coating (or the inner layer is made from materials having lubricious properties) that facilitate the movement one or more components of the energy absorbing system 44 within the sheath without binding, pinching, or otherwise limiting movement of the system within the sheath.

Turning now to FIGS. 38A-E, various approaches to forming ends 350, 352 of the sheath 61 are outlined. The sheath 61 can be formed from a tube and then cut to length. Sealing closed the ends 350, 352 of the tube can be accomplished in a number of ways and different ends of the sheath can be sealed differently depending on needs. An arc seal with strain relief 370 is depicted in FIG. 38A whereas an arc seal with increased surface area 372 is shown in FIG. 38B. Further alternate approaches are illustrated in FIGS. 38C-E where the arc seal is dashed, continuous or formed by dots. It is to be noted that folding of sheath material at the ends can be accomplished to form a soft edge such as by configuring one layer of the sheath over another and then sealing the ends closed.

Figure 40:
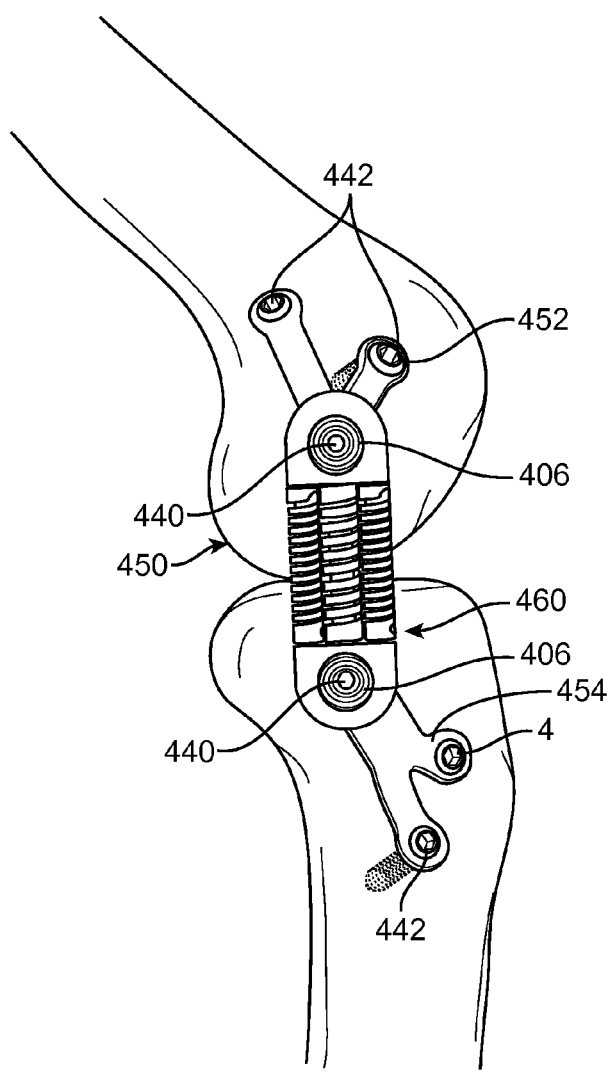
FIG. 40 is a medial perspective view of an implantable energy manipulation system.
Figure 41:
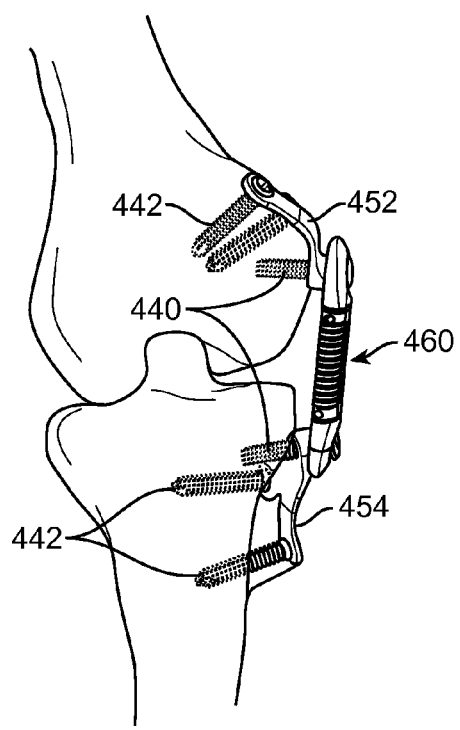
FIG. 41 is a posterior perspective view the system of FIG. 40.

FIGS. 40 and 41 illustrate an alternative embodiment of an energy absorbing system 450 is shown with proximal 452 and distal 454 bases. The bases 452, 454 are each Y-shaped low profile components designed to minimize the footprint and profile of the bases on the bone. Portions of the bases are contoured to match potential mounting surfaces of the femur and tibia. Also shown is an energy absorbing device 460 that is configured between and mounted to the bases in a manner similar to the systems described previously. The energy absorbing device 460 includes spherical bearings 406 which allow three degrees of motion between the absorber 460 an the bases 452, 454. A bone screw 440 is inserted in each end of the absorber 460 though the spherical bearing 406 and though the base 452, 454 to secure the absorber and the base to the bone. Two additional bone screws 442 are inserted in the legs of the Y-shaped bases.

Figure 42:
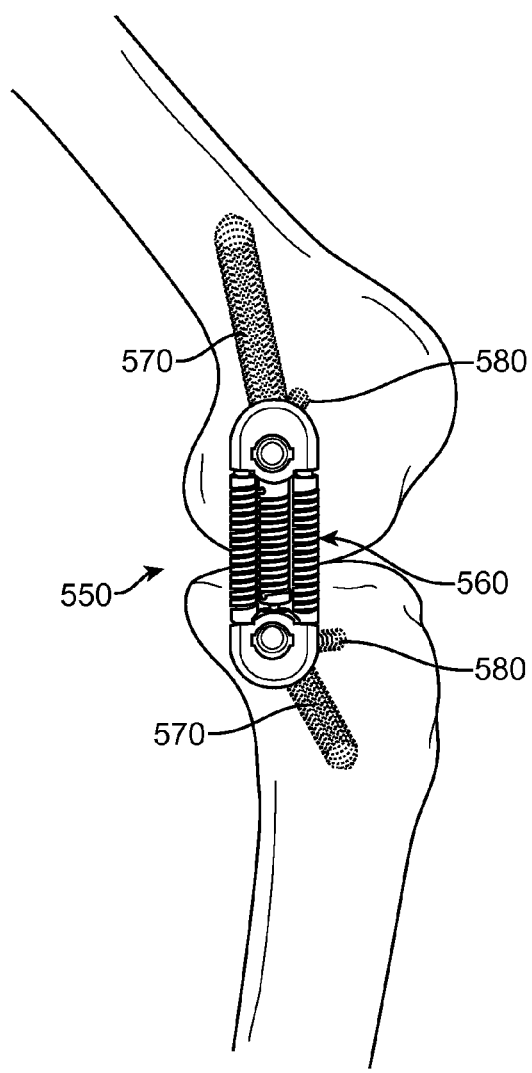
FIG. 42 is a medial perspective view of an alternative implantable energy manipulation system.
Figure 43:
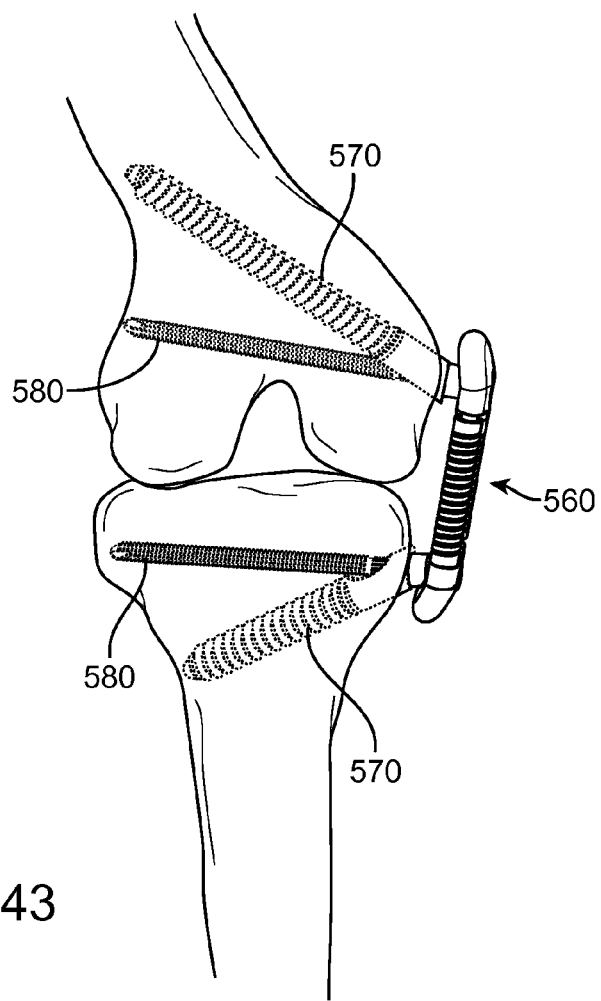
FIG. 43 is a posterior perspective view of the system of FIG. 42.

FIGS. 42 and 43 illustrate an alternative embodiment of an energy absorbing system 550 in which the bases of the previous embodiments are eliminated and the absorber 560 is secured on opposite ends to the bones of the knee joint by a set of bone anchors. The bone anchors include a long headless threaded bone anchor 570 which may include an internal feature for engagement with a torque driver, such as an internal hex feature. The long bone anchors 570 have angled holes at the top end for receiving a second shorter bone anchor or screw 580. The bone screw 580 extends through the spherical bearings of the absorber 560, through the long bone anchor 570 and into the bone. The two bone anchors 570, 580 are arranged at an acute angle with respect to one another and may be uni-cortical, bi-cortical, compression or locking screws. One or more spacers may be provided between the long bone anchor 570 and the absorber 560 to achieve a desired offset of the absorber from the joint to ensure that the absorber does not impinge on the joint though a full range of motion of the knee joint.

Although the embodiments of the energy absorbing systems described herein have been shown with two or three bone anchors in each of the femoral and tibial bones, it should be understood that other numbers of bone anchors or screws may be employed. For example for an energy absorbing system which is designed to unload only 10-20 pounds of load on the joint, anchoring the absorber to the bone with a single bone anchor may be desirable. In contrast, for a larger load, such as 40-50 pounds three to four bone anchors may be desirable.

In a contemplated method, the energy absorbing device 60 can be initially configured to eliminate or reduce loads to a desired degree, and to be later adjusted or altered as patient needs are better determined or change. Accordingly, post-operative alterations are contemplated as are adjustments resulting from changing the diameter of a dampening component or a spring rate of a device. In this regard, it is also contemplated there be no initial or load manipulation until the interventional site heals and the device is firmly implanted or during an initial treatment episode to substantially reduce the effects and pain associated with a patient afflicted with osteoarthritis for a long time. The device can provide distraction forces and carry all of the load to an extent that the joint surfaces do not experience load when the joint is fully load bearing. This distraction can continue for up to three months (or preferably two months) and then later the device can be adjusted to accomplish energy absorption without distraction. Moreover, as needs change, the method can involve removal or replacement of one or more components of the energy absorbing assembly. Further, various degrees of non-invasive approaches can be employed as is practical for a given interventional procedure.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims. In that regard, various features from certain of the disclosed embodiments can be incorporated into other of the disclosed embodiments to provide desired structure.

We claim:

1. An implantable system for manipulating energy transferred by members defining a knee joint including ligaments attached there across, comprising:
   a first attachment structure configured to be attached to a first member of the joint;
   a second attachment structure configured to be attached to a second member of the joint; and
   an absorber attached to the first attachment structure and second attachment structure, the absorber including three springs;
   wherein energy manipulated by the absorber is in a direction opposite from any forces absorbed by the ligaments;
   wherein a first spring and a second spring of the three springs has a first diameter and wherein a third spring is larger than two of the springs.

2. The system of claim 1, wherein the joint is a knee joint affected with osteoarthritis and variable amounts of energy absorption occurs while the bones of the knee joint follow their path of motion.

3. An implantable system for manipulating energy transferred by members defining a knee joint including ligaments attached there across, comprising:
   a first attachment structure configured to be attached to a first member of the joint;
   a second attachment structure configured to be attached to a second member of the joint; and
   an absorber attached to the first attachment structure and second attachment structure, the absorber including three springs;
   wherein energy manipulated by the absorber is in a direction opposite from any forces absorbed by the ligaments;
   wherein the first and second springs are attached to a first end of the absorber and wherein the third spring is attached to a second end of the absorber.

4. An implantable system for manipulating energy transferred by members defining a knee joint including ligaments attached there across, comprising: a first attachment structure configured to be attached to a first member of the joint; a second attachment structure configured to be attached to a second member of the joint; at least one screw for securing one of the first and second attachment structures to bone of the knee joint; and an absorber attached to the first attachment structure and second attachment structure, the absorber including at least one spring and at least one spherical bearing; wherein the absorber applies a force to the bones of the joint in a direction opposite from restraining forces applied by the ligaments of the joint; wherein said at least one screw passes through the at least one spherical bearing and through one of the first and second attachment structures to secure the absorber to said bone of the knee joint; and wherein the absorber includes a first socket that receives the at least one spherical bearing.

5. The system of claim 4, wherein the first attachment structure includes a first projection forming a first cone.

6. The system of claim 5, wherein the first cone extends into the spherical bearing.

7. The system of claim 6, further comprising a second spherical bearing; wherein the second attachment structure includes a second projection forming a second cone, and wherein the second cone extends into said second spherical bearing.

8. The system of claim 4, wherein the at least one spherical bearing includes a first spherical bearing spaced from a second spherical bearing.

9. The system of claim 8, wherein said at least one screw comprises first and second bone screws extending through each of the first and second spherical bearings and through the first and second attachment structures, respectively, to secure the absorber to said bone of the knee joint.

* * * * *